United States Patent [19]
Presta et al.

[11] Patent Number: 5,965,709
[45] Date of Patent: Oct. 12, 1999

[54] IGE ANTAGONISTS

[75] Inventors: Leonard G. Presta, San Francisco; Paula M. Jardieu, Berkeley, both of Calif.

[73] Assignee: Genentech, Inc., So. San Francisco, Calif.

[21] Appl. No.: 08/232,539

[22] Filed: Apr. 21, 1994

Related U.S. Application Data

[63] Continuation-in-part of application No. 08/178,583, Jan. 7, 1994, abandoned, which is a continuation of application No. 07/744,768, Aug. 14, 1991, abandoned.

[51] Int. Cl.$^6$ ................................................. C12D 21/08
[52] U.S. Cl. .................................... 530/387.3; 530/387.1; 530/388.15; 530/388.22
[58] Field of Search ............................. 530/387.1, 387.3, 530/388.15, 388.22

[56] References Cited

U.S. PATENT DOCUMENTS

| | | | |
|---|---|---|---|
| 4,161,522 | 7/1979 | Hamburger | ............................. 424/177 |
| 4,714,759 | 12/1987 | Whitaker, Jr. | . |
| 4,861,579 | 8/1989 | Meyer, Jr. et al. | . |
| 4,940,782 | 7/1990 | Rup et al. | . |

FOREIGN PATENT DOCUMENTS

| | | |
|---|---|---|
| 255249 | 2/1988 | European Pat. Off. . |
| 263655 | 4/1988 | European Pat. Off. . |
| 156285 | 7/1983 | Japan . |
| WO 89/04834 | 6/1989 | WIPO . |
| WO 89/06138 | 7/1989 | WIPO . |

OTHER PUBLICATIONS

Baniyash and Eshhar, "Inhibition of IgE binding to mast cells and basophils by monoclonal antibodies to murine IgE"; *Eur. J. Immunol.*, 14: 799–807 (1984).
Baniyash et al., "Anti–I GE monoclonal antibodies directed at the Fc$_\epsilon$ receptor binding site", *Molecular Immunology*, 25(8): 705–711 (1988).
Burt and Stanworth, "Inhibition of binding rat to IgE to rat mast cells by synthetic IgE peptides"*Eur. J. Immunol*, 17: 437–440 (1987).
Conrad, D. H., "Fc$_\epsilon$RII/CD23: The low affinity receptor for IgE", *Ann. Rev. Immunol.*, 8: 623–645 (1990).
Conrad et al., "The interaction of human and rodent IgE with the human basophil IgE receptor", *J. of Immunol.*, 130(1): 327–333 (1983).
Burt et al., "Analysis of the interaction between rat immunoglobulin E and rat mast cells using anti–peptide antibodies", *Mol. Immunol.*, 24(4): 379–389 (1987).
Disenhofer, "Crystallographic refinement and atomic models of a human Fc fragment and its complex with fragment B of protein A from *Staphylococcus aureus* at 2.9–and 2.8–Å resolution", *Biochemistry*, 20(9): 2361–2370 (1981).
Riske, F. et al.,"High affinity human IgE receptor(FcERI)", *J. Biol. Chem.*, 266(17): 11245–11251 (1991).

Liu, F.T. et al., "Expression of a biologically active fragment of human IgE epsilon chain in *Escherichia coli*,", *Proc. Natl. Acad. Sci.*, 81: 5369–5373 (1984).
Kurokawa, T. et al., "Expression of human immunoglobulin espilon chain cDNA in *E coli*", *Nucleic Acid Res.*, 11(10):3077–3085 (1983).
Geha, R.S. et al., "IgE sites relevant for binding to type 1 Fc epsilon (FCER) receptors on mast cells", *J. of Allergy & Clin. Immunol.*, 79(1): abstract, p. 129, No. 20 (1987).
Hakimi et al., "The α subunit of the human IgE receptor (FcERI) is sufficient for high affinity IgE binding", *J. Biol. Chem.*, 265(3): 22079–22081 (1990).
Helm et al., "The mast cell binding site on human immunoglobulin E," *Nature*, 331: 180–183 (1988).
Helm et al., "Blocking of passive sensitization of human mast cells and basophil granulocytes with IgE antibodies by a recombinant human ε–chain fragment of 76 amino acids", *Proc. Natl. Acad. Sci.*, 86:9465–9469 (1989).
Kulczycki, Jr. et al., "The interaction of IgE with rat basophilic leukemia cells I. Evidence for specific binding of IgE", *J. Exp. Med.*, 139: 600–616 (1974).
Nio et al., "Inhibition of histamine release by synthetic human IgE peptide fragments: structure–activity studies", *Peptide Chemistry*, 203–208 (1989).
Nissim et al., "Mapping of the high affinity Fc$_\epsilon$ receptor binding site to the third constant region domain of IgE", *EMBO*, 101–107 (1991).
Nitta et al., "Preliminary trial of specific targeting against malignant glioma", *Lancet*, 368–371 (1990).
Padlan & Davies, "A model of the Fc of immunoglobulin E", *Mol. Immunol.*, 23(10): 1063–1075 (1986).
Robertson & Liu, "IgE structure–function relationships defined by sequence directed antibodies induced by synthetic peptides", *Mol. Immunol.*, 25(2): 103–113 (1988).
Schwarzbaum et al., "Mapping of murine IgE epitopes involved in IgE–Fc$_\epsilon$ receptor interactions",*Eur. J. Immunol.*, 19:1015–1023 (1989).
Stanworth et al.,"Synthetic peptides comprising sequences of the human immunoglobulin E heavy chain capable of releasing histamine", *Biochem. J.*, 180: 665–668 (1979).
Stanworth et al., "The use of synthetic peptides in the delineation of immunoglobulin antigenic epitopes and Fc effector functions", *CIBA Found, Symp.*, 119: 226–244 (1986).
Vercelli et al., "The B–cell binding site on human immunoglobulin E", *Nature*, 338: 649–651 (1989).

(List continued on next page.)

*Primary Examiner*—Christina Y. Chan
*Assistant Examiner*—Patrick J. Nolan
*Attorney, Agent, or Firm*—Craig G. Svoboda

[57] ABSTRACT

IgE antagonists comprising one or more of the Fc$_\epsilon$RI receptor-binding determinant sites of human IgE are described. The disclosed antagonists include IgE variants, peptide antagonists, peptidomimetics and other small molecules. The antagonists are useful in raising and screening anti-IgE antibodies, in the isolation and purification of Fc$_\epsilon$RI receptor, and in the treatment of allergic disease.

8 Claims, 2 Drawing Sheets

OTHER PUBLICATIONS

Weetall et al., "Mapping the site of interaction between murine IgE and its high affinity receptor with chimeric Ig", *J. of Immunol.,* 145(11): 3849–3854 (1990).

Ishizaka, K., "Immunoglobulin E (IgE)", *Methods in Enzymology,* 116(Part II):76–94 (1985).

Hoffman, D. R., "Enzyme–linked immunosorbent assays (ELISA) for immunoglobulin E and blocking and antibodies", *Methods in Enzymology,* chapter 45, 73: 656–666 (1981).

Neurath, A. R., "Use of $^{125}$I–labeled anti–2,4–dinitrophenyl (DNP) antibodies as a general tracer in solid–phase radioimmunoassays", *Methods in Enzymology,* 73:127–138 (1981).

Tung, A. S., "Production, purification, and characterization of antigen–specific murine monoclonal antibodies of IgE class", *Methods in Enzymology,* chapter 6, 92:47–66 (1983).

Metzger & Kinet, "How antibodies work: focus on Fc receptors", *FASEB J.,* 2(1): 3–11 (1988).

Hook et al., "Monoclonal Antibodies Defining Epitopes on IgE", BASOPHILS, MAST CELLS, and IgE II, abst 6008 (1987).

Lazar et al., Transforming Growth Factor α: Mutation of Aspartic Acid 47 and Leucine 48 Results in Different Biological Activities, *Molecular and Cellular Biology* 8(3): 1247–1252 (1988).

Tao et al., Role of Carbohydrate in the Structure and Effector Functions Mediated by the Human IgG Constant Region, *J. Immunol.* 143(8): 2595–2601 (1989).

Burgess et al., "Possible Dissociation of the Heparin–binding and Mitogenic Activities of Heparin–binding (Acidic Fibroblast) Growth Factor–1 from Its Receptor–binding Activities by Site–directed Mutagenesis of a Single Lysine Residue", *J. Cell Biol.* 111: 2129–2138 (1990).

Glennie et al. "Preparation and Performance of Bispecific F(ab'γ)$_2$ Antibody Containing Thioether–Linked Fab'γ Fragments", *J. Immunol.* 139(7): 2367–2375 (1987).

Hook et al., "Monoclonal Antibodies Defining Epitopes on Human IgE" *Mol. Immunol.* 28(6): 631–639 (1991).

Kabat, *Sequence of Proteins Immunological Intent,* 4th Edition, Table of Contents, pp. 41–42, 167–168 (1987).

Queen et al., "A humanized antibody that binds to the interleukin 2 receptor", *PNAS USA* 88: 10029–10033 (1989).

Nissim et al., "Fine specificity of the IgE Interaction with the Low and High Affinity Fc Receptor", *J. Immunol.,* 150: 1365–1374 (1993).

A. R. Duncan et al., "Localization of the binding site for the human high–affinity Fc receptor on IgG", *Nature* 332: 563–564 (1988).

R. Jefferis et al., "Molecular Definition of Interaction Sites on Human IgG for Fc Receptors (huFcγR)", *Mol. Immunol.* 27: 1237–1240 (1990).

Kabat, *Sequence of Proteins of Immunological Intent,* 5th Edition, vol. 1, pp. 662–663, 671–672, 680–681, 689–690, 697, 701–702, 710, 719–720, 2275–2276 (1991).

Riechmann et al., Nature, 332, 24. Mar. 1988. pp. 323–327.

Kumar et al., P.N.A.S. USA, vol. 87:1337–1341, Feb. 1990.

Rudikoff et al., P.N.A.S. USA, vol. 79: 1979–1983, Mar. 1982.

Schwarzbaum et al., Eur. J. Immunol. vol. 19, 1015–1023, Jun. 1989.

Nissim et al., Methods., vol. 8, 124–132, Mar. 1995.

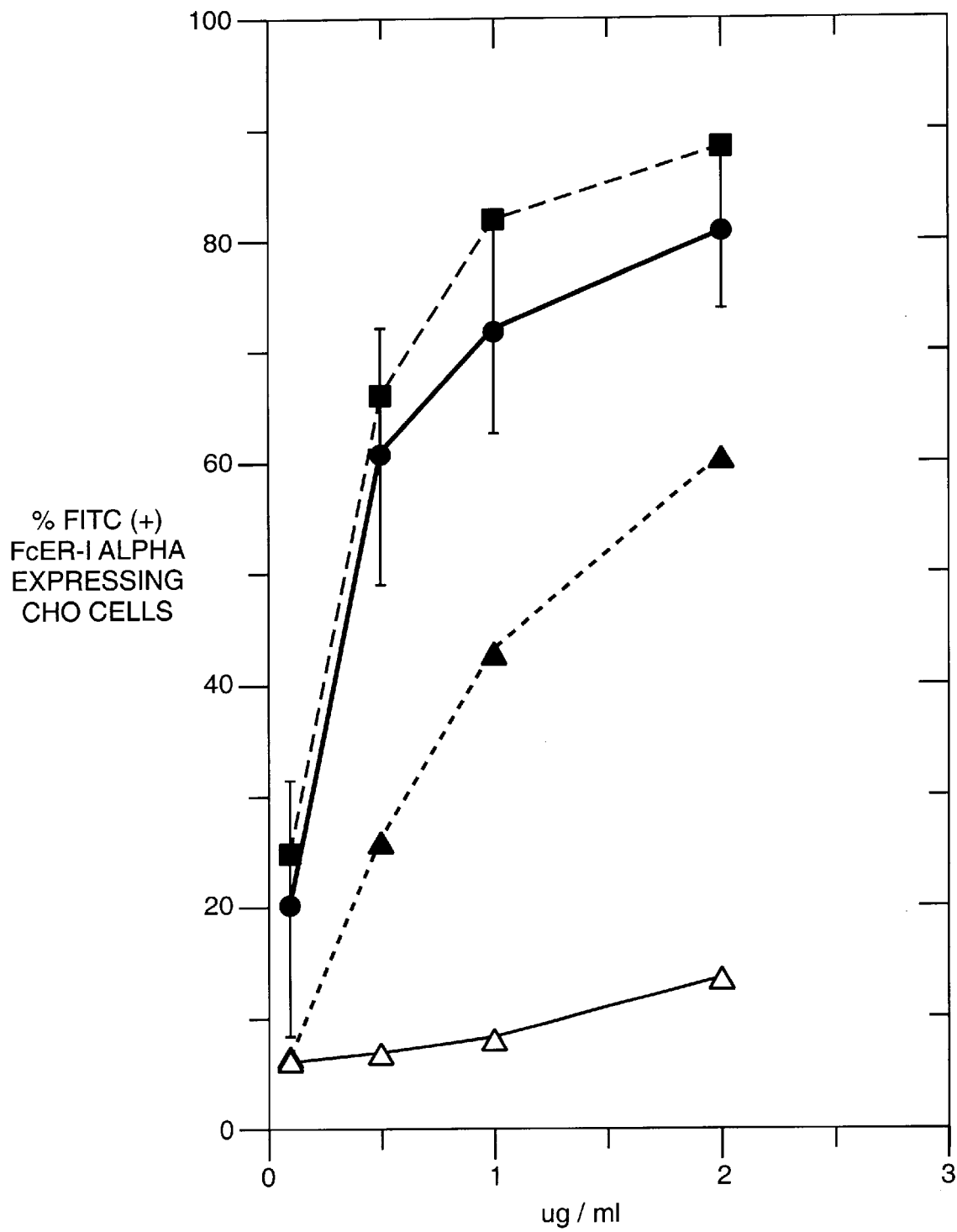
FIG._1

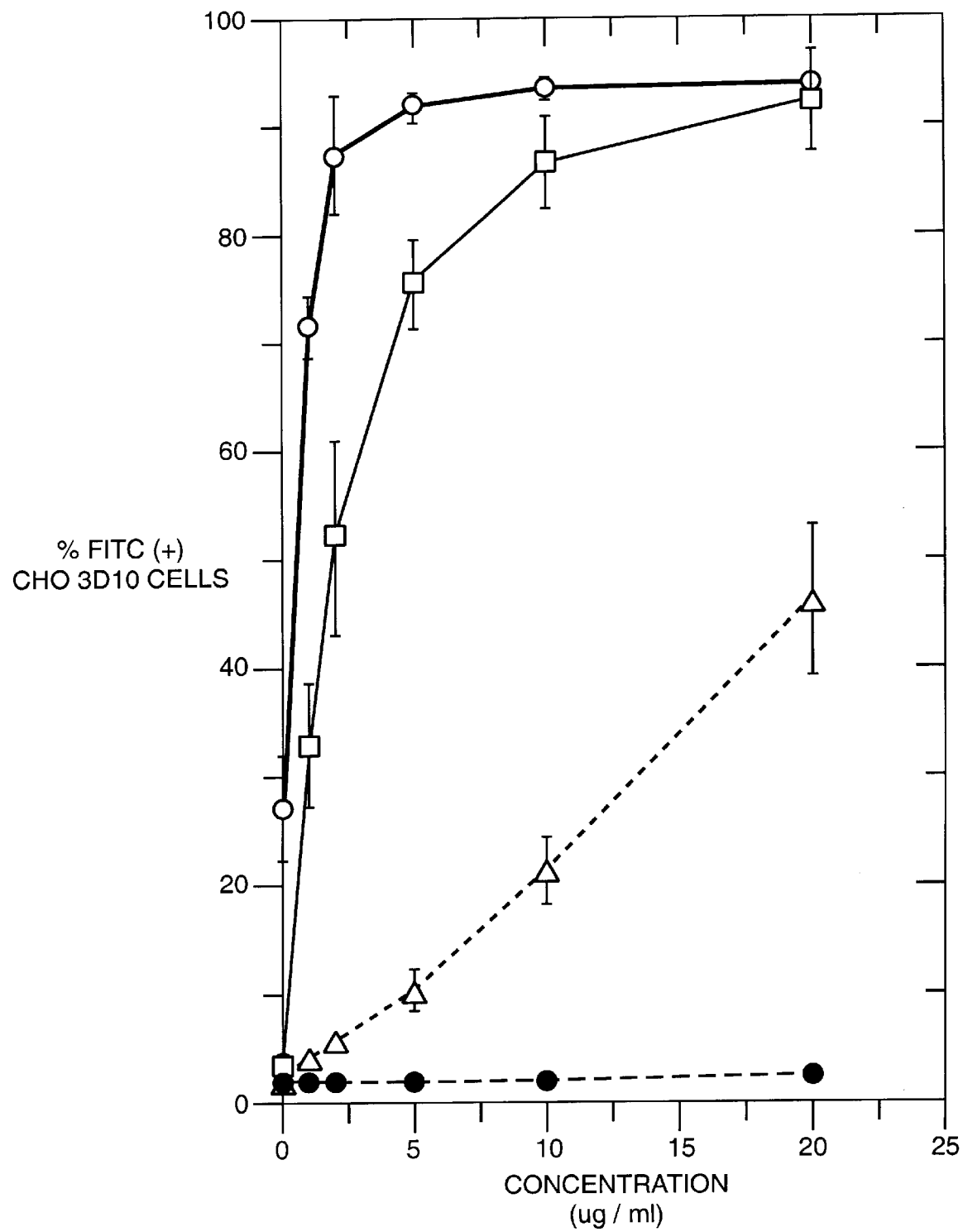
FIG._2

SEQUENCE LISTING

```
(1) GENERAL INFORMATION:

(iii) NUMBER OF SEQUENCES: 60

(2) INFORMATION FOR SEQ ID NO:1:

(i) SEQUENCE CHARACTERISTICS:
          (A) LENGTH: 5 amino acids
          (B) TYPE: Amino Acid
          (D) TOPOLOGY: Linear (xi) SEQUENCE DESCRIPTION: SEQ ID NO:1:

Arg Ala Ser Gly Lys
  1               5

(2) INFORMATION FOR SEQ ID NO:2:

(i) SEQUENCE CHARACTERISTICS:
          (A) LENGTH: 6 amino acids
          (B) TYPE: Amino Acid
          (D) TOPOLOGY: Linear (xi) SEQUENCE DESCRIPTION: SEQ ID NO:2:
```

```
Arg Ala Ser Gly Lys Pro
1               5   6
```

(2) INFORMATION FOR SEQ ID NO:3:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:3:

```
Arg Ala Ser Gly Lys Pro Val
1               5       7
```

(2) INFORMATION FOR SEQ ID NO:4:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:4:

```
Arg Ala Ser Gly Lys Pro Val Asn
1               5           8
```

(2) INFORMATION FOR SEQ ID NO:5:

(i) SEQUENCE CHARACTERISTICS:
        (A) LENGTH: 9 amino acids
        (B) TYPE: Amino Acid
        (D) TOPOLOGY: Linear (xi) SEQUENCE DESCRIPTION: SEQ ID NO:5:

```
Arg Ala Ser Gly Lys Pro Val Asn His
1               5               9
```

(2) INFORMATION FOR SEQ ID NO:6:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO:6:

```
Arg Ala Ser Gly Lys Pro Val Asn His Ser
1               5                   10
```

(2) INFORMATION FOR SEQ ID NO:7:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:7:

```
Ser Arg Ala Ser Gly Lys Pro
1               5       7
```

(2) INFORMATION FOR SEQ ID NO:8:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:8:

```
Ser Arg Ala Ser Gly Lys Pro Val
```

```
   1               5          8
```

(2) INFORMATION FOR SEQ ID NO:9:

(i) SEQUENCE CHARACTERISTICS:
        (A) LENGTH: 9 amino acids
        (B) TYPE: Amino Acid
        (D) TOPOLOGY: Linear (xi) SEQUENCE DESCRIPTION: SEQ ID NO:9:

```
Ser Arg Ala Ser Gly Lys Pro Val Asn
  1               5              9
```

(2) INFORMATION FOR SEQ ID NO:10:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO:10:

```
Ser Arg Ala Ser Gly Lys Pro Val Asn His
  1               5                  10
```

(2) INFORMATION FOR SEQ ID NO:11:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO:11:

```
Ser Arg Ala Ser Gly Lys Pro Val Asn His Ser
  1               5                  10  11
```

(2) INFORMATION FOR SEQ ID NO:12:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:12:

```
Asp Trp Ile Glu Gly Glu Thr
  1               5       7
```

(2) INFORMATION FOR SEQ ID NO:13:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:13:

```
Arg Asp Trp Ile Glu Gly Glu Thr
  1               5           8
```

(2) INFORMATION FOR SEQ ID NO:14:

(i) SEQUENCE CHARACTERISTICS:
        (A) LENGTH: 9 amino acids
        (B) TYPE: Amino Acid
        (D) TOPOLOGY: Linear (xi) SEQUENCE DESCRIPTION: SEQ ID NO:14:

```
Thr Arg Asp Trp Ile Glu Gly Glu Thr
  1               5               9
```

(2) INFORMATION FOR SEQ ID NO:15:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:15:

Arg Ala Leu Met
 1           4

(2) INFORMATION FOR SEQ ID NO:16:

(i) SEQUENCE CHARACTERISTICS:
        (A) LENGTH: 41 amino acids
        (B) TYPE: Amino Acid
        (D) TOPOLOGY: Linear (xi) SEQUENCE DESCRIPTION: SEQ ID NO:16:

Ser Arg Ala Ser Gly Lys Pro Val Asn His Ser Thr Arg Lys Glu
 1               5                  10                  15

Glu Lys Gln Arg Asn Gly Thr Leu Thr Val Thr Ser Thr Leu Pro
                20                  25                  30

Val Gly Thr Arg Asp Trp Ile Glu Gly Glu Thr
                35                  40  41

(2) INFORMATION FOR SEQ ID NO:17:

(i) SEQUENCE CHARACTERISTICS:
        (A) LENGTH: 40 amino acids
        (B) TYPE: Amino Acid
        (D) TOPOLOGY: Linear (xi) SEQUENCE DESCRIPTION: SEQ ID NO:17:

Arg Ala Ser Gly Lys Pro Val Asn His Ser Thr Arg Lys Glu Glu
 1               5                  10                  15

Lys Gln Arg Asn Gly Thr Leu Thr Val Thr Ser Thr Leu Pro Val
                20                  25                  30

Gly Thr Arg Asp Trp Ile Glu Gly Glu Thr
                35                  40

(2) INFORMATION FOR SEQ ID NO:18:

(i) SEQUENCE CHARACTERISTICS:
        (A) LENGTH: 56 amino acids
        (B) TYPE: Amino Acid
        (D) TOPOLOGY: Linear (xi) SEQUENCE DESCRIPTION: SEQ ID NO:18:

Ser Arg Ala Ser Gly Lys Pro Val Asn His Ser Thr Arg Lys Glu
 1               5                  10                  15

Glu Lys Gln Arg Asn Gly Thr Leu Thr Val Thr Ser Thr Leu Pro
                20                  25                  30

Val Gly Thr Arg Asp Trp Ile Glu Gly Glu Thr Tyr Gln Cys Arg
                35                  40                  45

Val Thr His Pro His Leu Pro Arg Ala Leu Met
                50                  55  56

(2) INFORMATION FOR SEQ ID NO:19:

(i) SEQUENCE CHARACTERISTICS:
        (A) LENGTH: 22 amino acids
        (B) TYPE: Amino Acid
        (D) TOPOLOGY: Linear (xi) SEQUENCE DESCRIPTION: SEQ ID NO:19:

Asp Trp Ile Glu Gly Glu Thr Tyr Gln Cys Arg Val Thr His Pro
1               5                   10                  15

His Leu Pro Arg Ala Leu Met
                20      22

(2) INFORMATION FOR SEQ ID NO:20:

(i) SEQUENCE CHARACTERISTICS:
        (A) LENGTH: 24 amino acids
        (B) TYPE: Amino Acid
        (D) TOPOLOGY: Linear (xi) SEQUENCE DESCRIPTION: SEQ ID NO:20:

Thr Arg Asp Trp Ile Glu Gly Glu Thr Tyr Gln Cys Arg Val Thr
1               5                   10                  15

His Pro His Leu Pro Arg Ala Leu Met
                20          24

(2) INFORMATION FOR SEQ ID NO:21:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:21:

Phe Asp Leu Phe Ile Arg Lys Ser
1               5           8

(2) INFORMATION FOR SEQ ID NO:22:

(i) SEQUENCE CHARACTERISTICS:
        (A) LENGTH: 9 amino acids
        (B) TYPE: Amino Acid
        (D) TOPOLOGY: Linear (xi) SEQUENCE DESCRIPTION: SEQ ID NO:22:

Lys Asp Thr Leu Met Ile Ser Arg Thr
1               5               9

(2) INFORMATION FOR SEQ ID NO:23:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:23:

Lys Asp Leu Met Ile Ser Arg Thr
1               5           8

(2) INFORMATION FOR SEQ ID NO:24:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:24:

Ala Pro Ser Lys Gly Thr
1               5   6

(2) INFORMATION FOR SEQ ID NO:25:

(i) SEQUENCE CHARACTERISTICS:
    (A) LENGTH: 6 amino acids
    (B) TYPE: Amino Acid
    (D) TOPOLOGY: Linear (xi) SEQUENCE DESCRIPTION: SEQ ID NO:25:

Ser His Glu Asp Pro Gln
1                5   6

(2) INFORMATION FOR SEQ ID NO:26:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:26:

Ser Pro Glu Asp Gly Gln
1                5   6

(2) INFORMATION FOR SEQ ID NO:27:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:27:

Ser Lys Gly Thr
1            4

(2) INFORMATION FOR SEQ ID NO:28:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:28:

Ala Ala Gly Ala
1            4

(2) INFORMATION FOR SEQ ID NO:29:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO:29:

Tyr Val Asp Gly Val Gln Val His Asn Ala Lys
1                5                   10  11

(2) INFORMATION FOR SEQ ID NO:30:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:30:

Ser Arg Ala Ser Gly Lys
1                5   6

(2) INFORMATION FOR SEQ ID NO:31:

(i) SEQUENCE CHARACTERISTICS:
        (A) LENGTH: 6 amino acids

```
            (B) TYPE: Amino Acid
            (D) TOPOLOGY: Linear (xi) SEQUENCE DESCRIPTION: SEQ ID NO:31:

Ala Ala Ala Ala Gly Ala
 1           5   6

(2) INFORMATION FOR SEQ ID NO:32:

(i) SEQUENCE CHARACTERISTICS:
            (A) LENGTH: 9 amino acids
            (B) TYPE: Amino Acid
            (D) TOPOLOGY: Linear (xi) SEQUENCE DESCRIPTION: SEQ ID NO:32:

His Gln Asp Trp Leu Asp Gly Lys Glu
 1           5               9

(2) INFORMATION FOR SEQ ID NO:33:

(i) SEQUENCE CHARACTERISTICS:
            (A) LENGTH: 4 amino acids
            (B) TYPE: Amino Acid
            (D) TOPOLOGY: Linear (xi) SEQUENCE DESCRIPTION: SEQ ID NO:33:

Glu Gly Glu Thr
 1           4

(2) INFORMATION FOR SEQ ID NO:34:

(i) SEQUENCE CHARACTERISTICS:
            (A) LENGTH: 4 amino acids
            (B) TYPE: Amino Acid
            (D) TOPOLOGY: Linear (xi) SEQUENCE DESCRIPTION: SEQ ID NO:34:

Ala Gly Ala Ala
 1           4

(2) INFORMATION FOR SEQ ID NO:35:

(i) SEQUENCE CHARACTERISTICS:
            (A) LENGTH: 4 amino acids
            (B) TYPE: Amino Acid
            (D) TOPOLOGY: Linear (xi) SEQUENCE DESCRIPTION: SEQ ID NO:35:

Ala Pro Ile Glu
 1           4

(2) INFORMATION FOR SEQ ID NO:36:

(i) SEQUENCE CHARACTERISTICS:
            (A) LENGTH: 6 amino acids
            (B) TYPE: Amino Acid
            (D) TOPOLOGY: Linear (xi) SEQUENCE DESCRIPTION: SEQ ID NO:36:

Lys Glu Glu Lys Gln Arg
 1           5   6

(2) INFORMATION FOR SEQ ID NO:37:

(i) SEQUENCE CHARACTERISTICS:
            (A) LENGTH: 6 amino acids
            (B) TYPE: Amino Acid
            (D) TOPOLOGY: Linear
```

(xi) SEQUENCE DESCRIPTION: SEQ ID NO:37:

Pro Arg Glu Gln Gln Tyr
1               5   6

(2) INFORMATION FOR SEQ ID NO:38:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:38:

Ala Glu Ala Lys Ala Arg
1               5   6

(2) INFORMATION FOR SEQ ID NO:39:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:39:

Lys Ala Glu Ala Gln Ala
1               5   6

(2) INFORMATION FOR SEQ ID NO:40:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:40:

Gln Cys Arg Val Thr
1               5

(2) INFORMATION FOR SEQ ID NO:41:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:41:

Ala Cys Ala Val Ala
1               5

(2) INFORMATION FOR SEQ ID NO:42:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:42:

Gln Lys His Trp Leu Ser Asp Arg
1               5               8

(2) INFORMATION FOR SEQ ID NO:43:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:43:

```
Ala Ala Ala Trp Leu Ala Ala Ala
1               5           8
```

(2) INFORMATION FOR SEQ ID NO:44:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:44:

```
Asp Ser Asn Pro Arg
1               5
```

(2) INFORMATION FOR SEQ ID NO:45:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:45:

```
Ala Ser Ala Pro Ala
1               5
```

(2) INFORMATION FOR SEQ ID NO:46:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:46:

```
Pro Arg Ala Ala
1           4
```

(2) INFORMATION FOR SEQ ID NO:47:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:47:

```
Gln Pro Arg Glu
1           4
```

(2) INFORMATION FOR SEQ ID NO:48:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:48:

```
Ala Ser Pro Ser Gln Thr
1               5   6
```

(2) INFORMATION FOR SEQ ID NO:49:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:49:

```
Leu His Asn His Tyr
```

```
            1               5

(2) INFORMATION FOR SEQ ID NO:50:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:50:

Ser Pro Ser Gln Thr
 1               5

(2) INFORMATION FOR SEQ ID NO:51:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:51:

Ala Pro Ala Ala Ala
 1               5

(2) INFORMATION FOR SEQ ID NO:52:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:52:

Ala Ala Leu Glu
 1           4

(2) INFORMATION FOR SEQ ID NO:53:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:53:

Cys Ala Asp Ser Asn Pro Arg
 1               5       7

(2) INFORMATION FOR SEQ ID NO:54:

(i) SEQUENCE CHARACTERISTICS:
        (A) LENGTH: 106 amino acids
        (B) TYPE: Amino Acid
        (D) TOPOLOGY: Linear (xi) SEQUENCE DESCRIPTION: SEQ ID NO:54:

Gly Val Ser Ala Tyr Leu Ser Arg Pro Ser Pro Phe Asp Leu Phe
 1               5                  10                  15

Ile Arg Lys Ser Pro Thr Ile Thr Cys Leu Val Val Asp Leu Ala
                20                  25                  30

Pro Ser Lys Gly Thr Val Asn Leu Thr Trp Ser Arg Ala Ser Gly
                35                  40                  45

Lys Pro Val Asn His Ser Thr Arg Lys Glu Glu Lys Gln Arg Asn
                50                  55                  60

Gly Thr Leu Thr Val Thr Ser Thr Leu Pro Val Gly Thr Arg Asp
                65                  70                  75

Trp Ile Glu Gly Glu Thr Tyr Gln Cys Arg Val Thr His Pro His
```

```
                         80                  85                  90
Leu Pro Arg Ala Leu Met Arg Ser Thr Thr Lys Thr Ser Gly Pro
                 95                 100                 105
Gly
106

(2) INFORMATION FOR SEQ ID NO:55:

(i) SEQUENCE CHARACTERISTICS:
        (A) LENGTH: 116 amino acids
        (B) TYPE: Amino Acid
        (D) TOPOLOGY: Linear (xi) SEQUENCE DESCRIPTION: SEQ ID NO:55:

Cys Pro Pro Cys Pro Ala Pro Glu Leu Leu Gly Gly Pro Ser Val
 1               5                  10                  15

Phe Leu Phe Pro Pro Lys Pro Lys Asp Thr Leu Met Ile Ser Arg
                20                  25                  30

Thr Pro Glu Val Thr Cys Val Val Asp Val Ser His Glu Asp
                35                  40                  45

Pro Glu Val Lys Phe Asn Trp Tyr Val Asp Gly Val Glu Val His
                50                  55                  60

Asn Ala Lys Thr Lys Pro Arg Glu Glu Gln Tyr Asn Ser Thr Tyr
                65                  70                  75

Arg Val Val Ser Val Leu Thr Val Leu His Gln Asp Trp Leu Asn
                80                  85                  90

Gly Lys Glu Tyr Lys Cys Lys Val Ser Asn Lys Ala Leu Pro Ala
                95                 100                 105

Pro Ile Glu Lys Thr Ile Ser Lys Ala Lys Gly
               110                 115 116

(2) INFORMATION FOR SEQ ID NO:56:

(i) SEQUENCE CHARACTERISTICS:
        (A) LENGTH: 113 amino acids
        (B) TYPE: Amino Acid
        (D) TOPOLOGY: Linear (xi) SEQUENCE DESCRIPTION: SEQ ID NO:56:

Cys Ala Asp Ser Asn Pro Arg Gly Val Ser Ala Tyr Leu Ser Arg
 1               5                  10                  15

Pro Ser Pro Phe Asp Leu Phe Ile Arg Lys Ser Pro Thr Ile Thr
                20                  25                  30

Cys Leu Val Val Asp Leu Ala Pro Ser Lys Gly Thr Val Asn Leu
                35                  40                  45

Thr Trp Ser Arg Ala Ser Gly Lys Pro Val Asn His Ser Thr Arg
                50                  55                  60

Lys Glu Glu Lys Gln Arg Asn Gly Thr Leu Thr Val Thr Ser Thr
                65                  70                  75

Leu Pro Val Gly Thr Arg Asp Trp Ile Glu Gly Glu Thr Tyr Gln
                80                  85                  90

Cys Arg Val Thr His Pro His Leu Pro Arg Ala Leu Met Arg Ser
                95                 100                 105

Thr Thr Lys Thr Ser Gly Pro Gly
               110                 113

(2) INFORMATION FOR SEQ ID NO:57:

(i) SEQUENCE CHARACTERISTICS:
```

(A) LENGTH: 11 amino acids
        (B) TYPE: Amino Acid
        (D) TOPOLOGY: Linear (xi) SEQUENCE DESCRIPTION: SEQ ID NO:57:

Cys Pro Pro Cys Pro Ala Pro Glu Leu Leu Gly
 1               5                   10  11

(2) INFORMATION FOR SEQ ID NO:58:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO:58:

Tyr Val Asp Gly Val Glu Val His Asn Ala Lys
 1               5                   10  11

(2) INFORMATION FOR SEQ ID NO:59:

(i) SEQUENCE CHARACTERISTICS:
        (A) LENGTH: 9 amino acids
        (B) TYPE: Amino Acid
        (D) TOPOLOGY: Linear (xi) SEQUENCE DESCRIPTION: SEQ ID NO:59:

His Gln Asp Trp Leu Asn Gly Lys Glu
 1               5                9

(2) INFORMATION FOR SEQ ID NO:60:

(i) SEQUENCE CHARACTERISTICS:
        (A) LENGTH: 105 amino acids
        (B) TYPE: Amino Acid
        (D) TOPOLOGY: Linear (xi) SEQUENCE DESCRIPTION: SEQ ID NO:60:

Gly Pro Ser Val Phe Leu Phe Pro Pro Lys Pro Lys Asp Thr Leu
 1               5                   10                  15

Met Ile Ser Arg Thr Pro Glu Val Thr Cys Val Val Val Asp Val
                20                  25                  30

Ser His Glu Asp Pro Glu Val Lys Phe Asn Trp Tyr Val Asp Gly
                35                  40                  45

Val Glu Val His Asn Ala Lys Thr Lys Pro Arg Glu Glu Gln Tyr
                50                  55                  60

Asn Ser Thr Tyr Arg Val Val Ser Val Leu Thr Val Leu His Gln
                65                  70                  75

Asp Trp Leu Asn Gly Lys Glu Tyr Lys Cys Lys Val Ser Asn Lys
                80                  85                  90

Ala Leu Pro Ala Pro Ile Glu Lys Thr Ile Ser Lys Ala Lys Gly
                95                  100                 105

IGE ANTAGONISTS

This is a continuation-in-part of U.S. Ser. No. 08/178, 583, filed Jan. 7, 1994, now abandoned, which is a continuation of U.S. Ser. No. 07/744,768, filed Aug. 14, 1991, now abandoned.

FIELD OF THE INVENTION

This invention relates to the field of immunoglobulin E (IgE) and to IgE antagonists.

BACKGROUND OF THE INVENTION

IgE is a member of the immunoglobulin family that mediates allergic responses such as asthma, food allergies, type 1 hypersensitivity and the familiar sinus inflammation suffered on a widespread basis. IgE is secreted by, and expressed on the surface of, B-cells. IgE binds to B-cells (and monocytes, eosinophils and platelets) through its Fc region to a low affinity IgE receptor ($Fc_\epsilon RII$). Upon exposure of a mammal to an allergen, B-cells synthesize IgE that binds the allergen. This IgE in turn is released into the circulation by the B-cells where it is bound by B-cells (through the $Fc_\epsilon RII$) and by mast cells and basophils through the so-called high affinity receptor ($Fc_\epsilon RI$) found on the surface of the mast cells and basophils. Such mast cells and basophils are thereby sensitized for allergen. The next exposure to the allergen cross-links the $Fc_\epsilon RI$ on these cells and thus activates their release of histamine and other factors which are responsible for clinical hypersensitivity and anaphylaxis.

It is generally understood that $Fc_\epsilon RI$ and $Fc_\epsilon RII$ bind to recognition sites in the IgE constant (Fc) domain. The IgE recognition sites for the two receptors have been poorly defined, despite considerable effort in the past directed to the problem.

Over the past decade several studies have been undertaken to determine which portions of the human IgE molecule are involved in binding to human $Fc_\epsilon RI$ and $Fc_\epsilon RII$ and which portions of the rodent IgE molecules are involved in binding to rodent $Fc_\epsilon RI$ and $Fc_\epsilon RII$. Essentially three approaches have been tried. First, peptides corresponding to specific portions of IgE sequence have been used as either competitive inhibitors of IgE-receptor binding or to elicit anti-IgE antibodies which would block IgE-receptor interaction. Second, mutations in IgE have been partially explored in efforts to identify the binding site. Third, chimeric molecules have been constructed in attempts to characterize the binding site. These three approaches are discussed below.

For purposes of consistency, all numbering of immunoglobulin amino acid residues, including the amino acid numbering of peptides corresponding to specific portions of IgE, mutant IgE molecules and chimeric IgE molecules, that appears herein is done according to the immunoglobulin amino acid residue numbering system of Kabat et al., *Sequences of Proteins of Immunological Interest* (National Institutes of Health, Bethesda, Md. 1987). Thus, any numbering system for immunoglobulins or fragments thereof appearing in the references discussed below is ignored and such immunoglobulins or fragments are renumbered herein according to the numbering system of Kabat et al.

In a study using the first approach discussed above, i.e., the IgE peptide approach, Nakamura et al., EP 0263655 published Apr. 13, 1988, found that peptides corresponding to human IgE residues 360–389, 457–523, 464–499, 516–521, 360–380, 376–388, 455–475, 464–472, 497–516, 513–526, 515–521, and 516–530 administered by injection into the skin of rats reduced the size of skin lesions caused by antigen challenge at the treated sites.

Helm et al., *Proc. Natl. Acad. Sci.*, 86:9465–9469 (1989) found that a peptide corresponding to IgE residues 329–409 blocked in vivo sensitization of human basophil granulocytes with human IgE antibodies. Further studies indicated that residues 395–409 were not essential for binding of the 329–409 peptide to $Fc_\epsilon RI$ (Helm et al., *Proc. Natl. Acad Sci.*, 86:9465–9469 (1989)).

Vercelli et al., *Nature*, 338:649–651 (1989) used recombinant IgE peptides as well as anti-$Fc_\epsilon$ monoclonal antibodies to investigate the B-cell ($Fc_\epsilon RII$) binding site of human IgE. They concluded that the $Fc_\epsilon RII$ binding site is in $Fc_\epsilon 3$ near K399-V402.

Burt et al., *Eur. J. Immun.*, 17:437–440 (1987) investigated seven peptides corresponding to amino acid sequences located within various surface regions of the $C_H 3$ and $C_H 4$ domains of rat IgE for competition against rat IgE in binding to rat mast cells. Their most active peptide, p129, was 1000-fold less active than IgE. p129 is homologous to human sequence 439–453 which includes loop EF. Another of their peptides, p130, homologous to residues 396–418 in the human $Fc_\epsilon 3$ domain, which includes the CD loop, had no activity.

Robertson et al., *Molec. Immun.*, 25:103–113 (1988) assessed murine IgE binding by sequence-directed antibodies induced by several synthetic peptides. They concluded that the sequence defined by their $\epsilon$-peptide-4 (homologous to human IgE residues 446–460 spanning the EF loop), was not significantly involved in receptor binding while the sequence defined by their E-peptide-3 (homologous to human IgE residues 387–401), was likely to be proximal to the IgE-receptor recognition site. Thus, the murine anti-IgE binding study of Robertson et al., *Molec. Immun.*, 25:103–113 (1988) contradicted the Burt et al., *Eur. J. Immun.*, 17:437–440 (1987) data implicating the EF loop in rat IgE binding.

Nio et al., *Peptide Chemistry*, 203–208 (1990) evaluated numerous peptides with respect to their ability to inhibit histamine release by human basophils in vitro. Only one peptide (peptide 2, Table 1), exhibited specific inhibition; this peptide encompassed residues 376–388. However, a larger peptide which incorporated this sequence (peptide 3, Table 1), had no inhibitory activity.

In a study using the second approach discussed above, i.e., mutations in mouse IgE to characterize the $Fc_\epsilon RI$-binding site on mouse IgE, Schwarzbaum et al., *Eur. J. Immun.*, 19:1015–1023 (1989) (supra) found that a point mutant P404H (P442H by the numbering system used herein) had 2-fold reduced affinity for $Fc_\epsilon RI$ on rat basophilic leukemia (RBL) cells, but the interpretation of this finding is controversial (Weetall et al., *J. Immunol.*, 145:3849–3854 (1990)).

Lastly, in the third approach discussed above, chimeric molecules have been constructed in attempts to identify the $Fc_\epsilon RI$-binding site on IgE. Human IgE does not bind to the murine receptor (Kulczycki Jr., et al., *J. Exp. Med.*, 139:600–616 (1974)) while rodent IgE binds to the human receptor with a reduced affinity (Conrad, et al., *J. Immun.*, 130:327–333 (1983)); human IgG1 does not bind to IgE receptors (Weetall et al., *J. Immun.*, 145:3849–3854 (1990)). Based on these observations, several groups have constructed human-murine chimeras or human IgE-IgG chimeras. Weetall et al., *J. Immun.*, 145:3849–3854 (1990) made a series of human IgG1-murine IgE chimeras and concluded that the Fc$_\epsilon$2 and Fc$_\epsilon$3 domains are involved in binding murine Fc$_\epsilon$RI while the Fc$_\epsilon$4 domain is unlikely to be involved in binding to murine Fc$_\epsilon$RI (but may possibly be involved in binding to Fc$_\epsilon$RII). However, these conclusions are uncertain since they rest primarily on lack of binding by chimeras and three of five chimeras lacked some interchain disulfide bonds.

Nissim et al., *EMBO J.*, 10:101–107 (1991) constructed a series of human-murine IgE chimeras and measured binding to RBL-2H3 rat mast cells and concluded that the portion of mouse IgE which binds with high affinity to the specialized Fcε receptor on RBL cells could be assigned to Fc$_\epsilon$3. In further studies with human-murine IgE chimeras, Nissim et al., *J. Immunol.*, 150: 1365–1374 (1993) reported that although the introduction of the entire mouse Fc$_\epsilon$3 domain into human IgE enabled the chimera to bind mouse Fc$_\epsilon$RI, the swapping of only 16 or 26 amino acids from the N-terminus of mouse Fc$_\epsilon$3 for the homologous residues in human IgE (residues 361–377 or 361–388) was insufficient to endow the chimera with mouse Fc$_\epsilon$RI-binding ability. Moreover, Nissim et al. (*J. Immunol.*) found that substitution of 26 amino acids from the N-terminus and 47 amino acids at the C-terminus of mouse Fc$_\epsilon$3 for the homologous residues in human IgE (residues 361–388 and 438–506) failed to confer mouse Fc$_\epsilon$RI-binding ability and also reduced human Fc$_\epsilon$RI-binding ability.

The results reported by these authors (e.g. Helm et al. and Burt et al.) are contradictory as to what part of IgE binds to Fc$_\epsilon$RI in rodents or humans. However, the instant invention precisely identifies the domains of human IgE which are involved in the binding of human IgE to human Fc$_\epsilon$RI receptor.

It is an object of this invention to identify antagonists of human IgE which are capable of inhibiting allergic responses.

It is another object to provide novel compounds for use in the assay of human Fc$_\epsilon$RI receptor and for use as immunogens or for selecting anti-human IgE antibodies.

SUMMARY OF THE INVENTION

Accordingly, the invention provides IgE antagonists that comprise one or more of the binding determinant sites in the Fc$_\epsilon$3 domain of human IgE, or comprise one or more fragments of such sites, variants of such sites or peptidomimetics of such sites.

One aspect of the invention is a compound of the formula

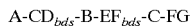

wherein:

A is absent or is any amino acid sequence from 1 to about 20 amino acids in length;

CD$_{bds}$ is absent or is an amino acid sequence selected from the group consisting of:

Arg-Ala-Ser-Gly-Lys (SEQ ID NO 1),
Arg-Ala-Ser-Gly-Lys-Pro (SEQ ID NO 2),
Arg-Ala-Ser-Gly-Lys-Pro-Val (SEQ ID NO 3),
Arg-Ala-Ser-Gly-Lys-Pro-Val-Asn (SEQ ID NO 4),
Arg-Ala-Ser-Gly-Lys-Pro-Val-Asn-His (SEQ ID NO 5),
Arg-Ala-Ser-Gly-Lys-Pro-Val-Asn-His-Ser (SEQ ID NO 6),
Ser-Arg-Ala-Ser-Gly-Lys-Pro (SEQ ID NO 7),
Ser-Arg-Ala-Ser-Gly-Lys-Pro-Val (SEQ ID NO 8),
Ser-Arg-Ala-Ser-Gly-Lys-Pro-Val-Asn (SEQ ID NO 9),
Ser-Arg-Ala-Ser-Gly-Lys-Pro-Val-Asn-His (SEQ ID NO 10), and
Ser-Arg-Ala-Ser-Gly-Lys-Pro-Val-Asn-His-Ser (SEQ ID NO 11);

B is absent or is any amino acid sequence from 1 to about 30 amino acids in length;

EF$_{bds}$ is absent or is an amino acid sequence selected from the group consisting of:

Asp-Trp-Ile-Glu-Gly-Glu-Thr (SEQ ID NO 12),
Arg-Asp-Trp-Ile-Glu-Gly-Glu-Thr (SEQ ID NO 13), and
Thr-Arg-Asp-Trp-Ile-Glu-Gly-Glu-Thr (SEQ NO ID 14);

C is absent or is any amino acid sequence from one to about 15 amino acids in length;

FG is absent or is Arg-Ala-Leu-Met (SEQ ID NO 15);

provided that at least one amino acid sequence in the group consisting of CD$_{bds}$, EF$_{bds}$ and FG is present in the compound.

The compounds of the invention are provided in linear or cyclized form and optionally comprise at least one amino acid residue that is not commonly found in nature or at least one amide isostere.

The invention also provides an IgE variant comprising one or more amino acid sequences selected from the group consisting of CD$_{bds}$, EF$_{bds}$, and Arg-Ala-Leu-Met (SEQ ID NO 15), wherein CD$_{bds}$ is selected from the group consisting of:
Arg-Ala-Ser-Gly-Lys (SEQ ID NO 1),
Arg-Ala-Ser-Gly-Lys-Pro (SEQ ID NO 2),
Arg-Ala-Ser-Gly-Lys-Pro-Val (SEQ ID NO 3),
Arg-Ala-Ser-Gly-Lys-Pro-Val-Asn (SEQ ID NO 4),
Arg-Ala-Ser-Gly-Lys-Pro-Val-Asn-His (SEQ ID NO 5),
Arg-Ala-Ser-Gly-Lys-Pro-Val-Asn-His-Ser (SEQ ID NO 6),
Ser-Arg-Ala-Ser-Gly-Lys-Pro (SEQ ID NO 7),
Ser-Arg-Ala-Ser-Gly-Lys-Pro-Val (SEQ ID NO 8),
Ser-Arg-Ala-Ser-Gly-Lys-Pro-Val-Asn (SEQ ID NO 9),
Ser-Arg-Ala-Ser-Gly-Lys-Pro-Val-Asn-His (SEQ ID NO 10), and
Ser-Arg-Ala-Ser-Gly-Lys-Pro-Val-Asn-His-Ser (SEQ ID NO 11); and EF$_{bds}$ is selected from the group consisting of:
Asp-Trp-Ile-Glu-Gly-Glu-Thr (SEQ ID NO 12),
Arg-Asp-Trp-Ile-Glu-Gly-Glu-Thr (SEQ ID NO 13), and
Thr-Arg-Asp-Trp-Ile-Glu-Gly-Glu-Thr (SEQ ID NO 14).

BRIEF DESCRIPTION OF THE FIGURES

FIG. 1 depicts the binding of human IgE and various amino acid substitution variants of human IgE to human Fc$_\epsilon$RI α-chain expressed on CHO 3D10 cells. Variant 42 (Glu452Gln), variant 43 (Glu452Asp), variant 70 (Asp361Ala/Asn363Ala/Arg365Ala), and human IgE are represented by open triangles, closed squares, closed triangles, and closed circles, respectively.

FIG. 2 depicts the binding of human IgE, human IgG, and chimeric immunoglobulins IgG2/E3 and IgGEL to human Fc$_\epsilon$RI α-chain expressed on CHO 3D10 cells. IgG2/E3, IgGEL, human IgE, and human IgG are represented by open squares, open triangles, open circles, and closed circles, respectively.

DETAILED DESCRIPTION OF THE INVENTION

A. Definitions

The term "IgE antagonist" as used herein is defined as any compound that (1) is capable of disrupting or blocking the interaction between human IgE and the high affinity receptor $Fc_\epsilon RI$ on human mast cells or basophils; (2) is capable of binding to the $Fc_\epsilon 3$ domain of human IgE; (3) contains an antigenic site that can be used in the raising of antibodies capable of binding to the $Fc_\epsilon 3$ domain of human IgE; (4) contains an antigenic site that can be used in the screening of antibodies capable of binding to the $Fc_\epsilon 3$ domain of human IgE; (5) contains an antigenic site that can be used in the raising of antibodies capable of disrupting or blocking the interaction between human IgE and the high affinity receptor $Fc_\epsilon RI$ on human mast cells or basophils; or (6) contains an antigenic site that can be used in the screening of antibodies capable of disrupting or blocking the interaction between human IgE and the high affinity receptor $Fc_\epsilon RI$ on human mast cells or basophils. IgE antagonists include IgE variants, IgE peptide antagonists, peptidomimetics and other small molecules.

As used herein, the term "peptide" is defined as an amino acid sequence from one amino acid to about 700 amino acids in length.

As used herein, the term "IgE variant" denotes any amino acid variant of human IgE, including amino acid substitution, deletion, and addition variants, or any combination thereof. The definition encompasses chimeric immunoglobulins such as human IgE/non-human immunoglobulin chimeras, including human IgE/non-human IgE, human IgE/non-human IgG, human IgE/non-human IgA, human IgE/non-human IgD, and human IgE/non-human IgM hybrid molecules. Additional IgE variants include cross-isotype chimeras, such as human IgE/human IgG, human IgE/human IgA, human IgE/human IgD, and human IgE/human IgM hybrid molecules. Also included in the definition is any fragment of an IgE variant molecule which comprises the variant or hybrid region(s) of the molecule.

In general, unless otherwise specified, the abbreviations used for the designation of amino acids and the protective groups used therefor are based on recommendations of the IUPAC-IUB Commission of Biochemical Nomenclature (*Biochemistry*, 11:1726–1732 (1972). The nomenclature used to define compounds of the invention is that specified by the IUPAC, published in *European Journal of Biochemistry*, 138:9–37 (1984).

B. General Methods

The IgE antagonists of the invention are based on the inventors' identification of the IgE domains involved in the binding of IgE to $Fc_\epsilon RI$ receptor. Thus, the invention provides IgE antagonists with molecular structures that duplicate or mimic one or more of the $Fc_\epsilon RI$-binding domains of IgE. The IgE antagonists of the invention include peptide antagonists, peptidomimetics and other small molecules, immunoglobulin variants, such as amino acid variants of human IgE including amino acid substitution, deletion, and addition variants, or any combination thereof, and chimeric immunoglobulins such as cross-species chimeras and cross-isotype chimeras.

I. IgE Peptide Antagonists

One embodiment of the invention is a peptide antagonist of IgE that comprises one or more of the IgE binding determinants. Such IgE binding determinants contain IgE amino acid residues that are critical for IgE binding to the $Fc_\epsilon RI$ receptor. The important IgE binding determinants are the CD, EF and FG loops located in the third constant domain of IgE, $Fc_\epsilon 3$.

Thus, the IgE peptide antagonists of the invention include a peptide corresponding to the amino acid sequence of the CD loop of $Fc_\epsilon 3$, namely, Ser-Arg-Ala-Ser-Gly-Lys-Pro-Val-Asn-His-Ser (SEQ ID NO 11) (amino acid residues 407–420 of IgE). Within the CD loop, amino acid residues 408 (Arg), 415 (Lys), and 411 (Ser) are the most important for IgE binding to $Fc_\epsilon RI$. Accordingly, preferred are IgE peptide antagonists that contain the CD loop core amino acid sequence formed by residues 408–415 of IgE, namely, Arg-Ala-Ser-Gly-Lys (SEQ ID NO 1). Also preferred are IgE peptide antagonists that contain a CD loop amino acid sequence that includes the core sequence, such as Arg-Ala-Ser-Gly-Lys-Pro (SEQ ID NO 2);
Arg-Ala-Ser-Gly-Lys-Pro-Val (SEQ ID NO 3);
Arg-Ala-Ser-Gly-Lys-Pro-Val-Asn (SEQ ID NO 4);
Arg-Ala-Ser-Gly-Lys-Pro-Val-Asn-His (SEQ ID NO 5);
Arg-Ala-Ser-Gly-Lys-Pro-Val-Asn-His-Ser (SEQ ID NO 6);
Ser-Arg-Ala-Ser-Gly-Lys-Pro (SEQ ID NO 7);
Ser-Arg-Ala-Ser-Gly-Lys-Pro-Val (SEQ ID NO 8);
Ser-Arg-Ala-Ser-Gly-Lys-Pro-Val-Asn (SEQ ID NO 9);
Ser-Arg-Ala-Ser-Gly-Lys-Pro-Val-Asn-His (SEQ ID NO 10); and
Ser-Arg-Ala-Ser-Gly-Lys-Pro-Val-Asn-His-Ser (SEQ ID NO 11).

In addition, the invention includes any amino acid sequence containing the CD loop core sequence wherein at least one amide bond in the amino acid sequence is replaced with an amide isostere. As used herein, the terms "$CD_{bds}$" and "CD loop binding determinant sequence" denote any amino acid sequence within the CD loop of $Fc_\epsilon 3$ that contains the CD loop core amino acid sequence (Arg-Ala-Ser-Gly-Lys) (SEQ ID NO 1), including every amino acid sequence in the group consisting of:

Arg-Ala-Ser-Gly-Lys (SEQ ID NO 1);
Arg-Ala-Ser-Gly-Lys-Pro (SEQ ID NO 2);
Arg-Ala-Ser-Gly-Lys-Pro-Val (SEQ ID NO 3);
Arg-Ala-Ser-Gly-Lys-Pro-Val-Asn (SEQ ID NO 4);
Arg-Ala-Ser-Gly-Lys-Pro-Val-Asn-His (SEQ ID NO 5);
Arg-Ala-Ser-Gly-Lys-Pro-Val-Asn-His-Ser (SEQ ID NO 6);
Ser-Arg-Ala-Ser-Gly-Lys-Pro (SEQ ID NO 7);
Ser-Arg-Ala-Ser-Gly-Lys-Pro-Val (SEQ ID NO 8);
Ser-Arg-Ala-Ser-Gly-Lys-Pro-Val-Asn (SEQ ID NO 9);
Ser-Arg-Ala-Ser-Gly-Lys-Pro-Val-Asn-His (SEQ ID NO 10); and
Ser-Arg-Ala-Ser-Gly-Lys-Pro-Val-Asn-His-Ser (SEQ ID NO 11).

wherein any amide bond (—C(═O)—NH—) in the $CD_{bds}$ may be replaced by an amide isostere selected from the group consisting of:
—CH$_2$—NH—,
—CH$_2$—S—,
—CH$_2$—S(O)$_n$—, where n is 1 or 2,
—CH$_2$—CH$_2$—,
—CH═CH— (E or Z),
—C(═O)—CH$_2$—,
—CH(CN)—NH—,
—C(OH)—CH$_2$—, and
—O—C(═O)—NH—

The invention further provides for an IgE peptide antagonist corresponding to the EF loop of $Fc_\epsilon 3$, namely, Thr-Arg-Asp-Trp-Ile-Glu-Gly-Glu-Thr (SEQ ID NO 14) (amino acid residues 445–453 of IgE). Within the EF loop, amino acid residues 447 (Asp), 452 (Glu), and 453 (Thr) are the most important for IgE binding to $Fc_\epsilon RI$. Accordingly, preferred are IgE peptide antagonists that contain the EF loop core amino acid sequence formed by residues 447–453 of IgE, namely, Asp-Trp-Ile-Glu-Gly-Glu-Thr (SEQ ID NO 12). Also preferred are IgE peptide antagonists that contain an EF loop amino acid sequence that includes the core sequence, such as Arg-Asp-Trp-Ile-Glu-Gly-Glu-Thr (SEQ ID NO 13). In addition, the invention includes any amino acid sequence containing the EF loop core sequence wherein at least one amide bond in the amino acid sequence is replaced with an amide isostere. As used herein, the terms "$EF_{bds}$" and "EF loop binding determinant sequence" denote any amino acid sequence within the EF loop of $Fc_\epsilon 3$ that contains the EF loop core amino acid sequence (Asp-TrpIle-Glu-Gly-Glu-Thr) (SEQ ID NO 12), including every amino acid sequence in the group consisting of:

Asp-Trp-Ile-Glu-Gly-Glu-Thr (SEQ ID NO 12);
Arg-Asp-Trp-Ile-Glu-Gly-Glu-Thr (SEQ ID NO 13); and
Thr-Arg-Asp-Trp-Ile-Glu-Gly-Glu-Thr (SEQ ID NO 14);

wherein any amide bond (—C(=O)—NH—) in the $EF_{bds}$ may be replaced by an amide isostere selected from the group consisting of:

—CH$_2$—NH—,
—CH$_2$—S—,
—CH$_2$—S(O)$_n$—, where n is 1 or 2,
—CH$_2$—CH$_2$—,
—CH=CH— (E or Z),
—C(=O)—CH$_2$—,
—CH(CN)—NH—,
—C(OH)—CH$_2$—, and
—O—C(=O)—NH—

The invention also encompasses an IgE peptide antagonist containing the FG loop of $Fc_\epsilon 3$, namely, Arg-Ala-Leu-Met (SEQ ID NO 15) (amino acid residues 465–469 of IgE) (SEQ ID NO 15). In addition, the invention includes any amino acid sequence containing the FG loop wherein at least one amide bond in the amino acid sequence is replaced with an amide isostere. As used herein, the terms "FG" and "FG loop binding determinant sequence" denote the amino acid sequence Arg-Ala-Leu-Met (SEQ ID NO 15). Also included in the definition is any isostere of the Arg-Ala-Leu-Met (SEQ ID NO 15) wherein any amide bond (—C(=O)—NH—) is replaced by an amide isostere selected from the group consisting of:

—CH$_2$—NH—,
—CH$_2$—S—,
—CH$_2$—S(O)$_n$—, where n is 1 or 2,
—CH$_2$—CH$_2$—,
—CH=CH— (E or Z),
—C(=O)—CH$_2$—,
—CH(CN)—NH—,
—C(OH)—CH$_2$—, and
—O—C(=O)—NH—

In another embodiment, the invention provides for IgE peptide antagonists that contain two or more IgE binding determinants linked together to form a molecule with increased ability to compete with IgE for binding to $Fc_\epsilon RI$. The important binding determinants can be joined without any intervening sequence, such as $CD_{bds}$-$EF_{bds}$, $CD_{bds}$-FG, $CD_{bds}$-$EF_{bds}$-FG, $CD_{bds}$-FG-$EF_{bds}$, $EF_{bds}$-FG, $EF_{bds}$-$CD_{bds}$, $EF_{bds}$-FG-$CD_{bds}$, $EF_{bds}$-$CD_{bds}$-FG, FG-$CD_{bds}$, FG-$EF_{bds}$, FG-$CD_{bds}$-$EF_{bds}$, and FG-$EF_{bds}$-$CD_{bds}$, Alternatively, the important binding determinants can be joined together with one or more intervening sequences between binding determinants. Thus, the invention includes IgE peptide antagonists of the form $CD_{bds}$-X-$EF_{bds}$, $CD_{bds}$-X-FG, $CD_{bds}$-X-$EF_{bds}$-FG, $CD_{bds}$-$EF_{bds}$-X-FG, $CD_{bds}$-X-$EF_{bds}$-Y-FG, $CD_{bds}$-X-FG-$EF_{bds}$, $CD_{bds}$-FG-X-$EF_{bds}$, $CD_{bds}$-X-FG-Y-$EF_{bds}$, $EF_{bds}$-X-FG, $EF_{bds}$-X-$CD_{bds}$, $EF_{bds}$-X-FG-$CD_{bds}$, $EF_{bds}$-FGX-$CD_{bds}$, $EF_{bds}$-X-FG-Y-$CD_{bds}$, $EF_{bds}$-X-$CD_{bds}$-FG, $EF_{bds}$-$CD_{bds}$-X-FG, $EF_{bds}$-X-$CD_{bds}$-Y-FG, FG-X-$CD_{bds}$, FG-X-$EF_{bds}$, FG-X-$CD_{bds}$-$EF_{bds}$, FG-$CD_{bds}$-X-$EF_{bds}$, FG-X-$CD_{bds}$-Y-$EF_{bds}$, FG-X-$EF_{bds}$-$CD_{bds}$, FG-$EF_{bds}$-X-$CD_{bds}$, and FG-X-$EF_{bds}$-Y-$CD_{bds}$, wherein X is any amino acid sequence from one to about 30 amino acids in length and Y is any amino acid sequence from one to about 30 amino acids in length.

In another embodiment, the invention provides for compounds represented by formula I:

$$A\text{-}CD_{bds}\text{-}B\text{-}EF_{bds}\text{-}C\text{-}FG \qquad (I)$$

wherein:

A is absent or is any amino acid sequence from 1 to about 20 amino acids in length;

$CD_{bds}$ is absent or is an amino acid sequence selected from the group consisting of:

Arg-Ala-Ser-Gly-Lys (SEQ ID NO 1);
Arg-Ala-Ser-Gly-Lys-Pro (SEQ ID NO 2);
Arg-Ala-Ser-Gly-Lys-Pro-Val (SEQ ID NO 3);
Arg-Ala-Ser-Gly-Lys-Pro-Val-Asn (SEQ ID NO 4);
Arg-Ala-Ser-Gly-Lys-Pro-Val-Asn-His (SEQ ID NO 5);
Arg-Ala-Ser-Gly-Lys-Pro-Val-Asn-His-Ser (SEQ ID NO 6);
Ser-Arg-Ala-Ser-Gly-Lys-Pro (SEQ ID NO 7);
Ser-Arg-Ala-Ser-Gly-Lys-Pro-Val (SEQ ID NO 8);
Ser-Arg-Ala-Ser-Gly-Lys-Pro-Val-Asn (SEQ ID NO 9);
Ser-Arg-Ala-Ser-Gly-Lys-Pro-Val-Asn-His (SEQ ID NO 10); and
Ser-Arg-Ala-Ser-Gly-Lys-Pro-Val-Asn-His-Ser (SEQ ID NO 11).

B is absent or is any amino acid sequence from 1 to about 30 amino acids in length;

$EF_{bds}$ is absent or is an amino acid sequence selected from the group consisting of:

Asp-Trp-Ile-Glu-Gly-Glu-Thr (SEQ ID NO 12);
Arg-A sp-Trp-Ile-Glu-Gly-Glu-Thr (SEQ ID NO 13); and
Thr-Arg-Asp-Trp-Ile-Glu-Gly-Glu-Thr (SEQ ID NO 14);

C is absent or is any amino acid sequence from one to about 15 amino acids in length;

FG is absent or is Arg-Ala-Leu-Met (SEQ ID NO 15);

provided that at least one amino acid sequence in the group consisting of $CD_{bds}$, $EF_{bds}$ and FG is present in the compound.

Preferred embodiments of the invention include formula I compounds that have at least one pair of IgE binding determinants connected by a glycine, serine, or combination glycine/serine bridge. In one class of such formula I compounds, B is a glycine bridge between a $CD_{bds}$ amino acid sequence and an $EF_{bds}$ amino acid sequence, and B is from 1 to about 30 glycine residues in length. In another class of such formula I compounds, C is a glycine bridge between an $EF_{bds}$ amino acid sequence and the amino acid sequence Arg-Ala-Leu-Met (SEQ ID NO 15), and C is from 1 to about 15 glycine residues in length.

Other preferred embodiments of the invention include IgE peptide antagonists of the formula $CD_{bds}$-X-$EF_{bds}$, $EF_{bds}$-

X-FG, and CD$_{bds}$-X-EF$_{bds}$-Y-FG, wherein X is a glycine bridge from about 1 to about 30 glycine residues in length and Y is a glycine bridge from about 1 to about 15 glycine residues in length. Particularly preferred are IgE peptide antagonists containing two or more important binding determinants linked by the natural amino acid sequence of IgE such that the antagonist is a fragment of Fc$_\epsilon$3. Such antagonists include Ser-Arg-Ala-Ser-Gly-Lys-Pro-Val-Asn-His-Ser-Thr-Arg-Lys-Glu-Glu-Lys-Gln-Arg-Asn-Gly-Thr-Leu-Thr-Val-Thr-Ser-Thr-Leu-Pro-Val-Gly-Thr-Arg-Asp-Trp-Ile-Glu-Gly-Glu-Thr (SEQ ID NO 16);

Arg-Ala-Ser-Gly-Lys-Pro-Val-Asn-His-Ser-Thr-Arg-Lys-Glu-Glu-Lys-Gln-Arg-Asn-Gly-Thr-Leu-Thr-Val-Thr-Ser-Thr-Leu-Pro-Val-Gly-Thr-Arg-Asp-Trp-Ile-Glu-Gly-Glu-Thr (SEQ ID NO 17);

Ser-Arg-Ala-Ser-Gly-Lys-Pro-Val-Asn-His-Ser-Thr-Arg-Lys-Glu-Glu-Lys-Gln-Arg-Asn-Gly-Thr-Leu-Thr-Val-Thr-Ser-Thr-Leu-Pro-Val-Gly-Thr-Arg-Asp-Trp-Ile-Glu-Gly-Glu-Thr-Tyr-Gln-Cys-Arg-Val-Thr-His-Pro-His-Leu-Pro-Arg-Ala-Leu-Met (SEQ ID NO 18);

Asp-Trp-Ile-Glu-Gly-Glu-Thr-Tyr-Gln-Cys-Arg-Val-Thr-His-Pro-His-Leu-Pro-Arg-Ala-Leu-Met (SEQ ID NO 19); and Thr-Arg-Asp-Trp-Ile-Glu-Gly-Glu-Thr-Tyr-Gln-Cys-Arg-Val-Thr-His-Pro-His-Leu-Pro-Arg-Ala-Leu-Met (SEQ ID NO 20).

The IgE peptide antagonists are provided as linear or conformationally restrained polypeptides. Conformational restraint is accomplished by cross-linking the polypeptide, for example, at the N- and C- termini so as to produce a cyclic structure. In a preferred embodiment the cyclic forms have one of the following structures:

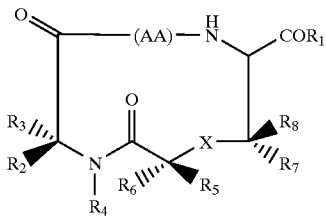

wherein AA is an amino acid sequence selected from the group consisting of: —(a1)—(CD$_{bds}$)—(a2)—, —(a1)—(EF$_{bds}$)—(a2)—, and —(a1)—(FG)—(a2)—;

CD$_{bds}$ is an amino acid sequence selected from the group consisting of:
Arg-Ala-Ser-Gly-Lys (SEQ ID NO 1);
Arg-Ala-Ser-Gly-Lys-Pro (SEQ ID NO 2);
Arg-Ala-Ser-Gly-Lys-Pro-Val (SEQ ID NO 3);
Arg-Ala-Ser-Gly-Lys-Pro-Val-Asn (SEQ ID NO 4);
Arg-Ala-Ser-Gly-Lys-Pro-Val-Asn-His (SEQ ID NO 5);
Arg-Ala-Ser-Gly-Lys-Pro-Val-Asn-His-Ser (SEQ ID NO 6);
Ser-Arg-Ala-Ser-Gly-Lys-Pro (SEQ ID NO 7);
Ser-Arg-Ala-Ser-Gly-Lys-Pro-Val (SEQ ID NO 8);
Ser-Arg-Ala-Ser-Gly-Lys-Pro-Val-Asn (SEQ ID NO 9);
Ser-Arg-Ala-Ser-Gly-Lys-Pro-Val-Asn-His (SEQ ID NO 10); and
Ser-Arg-Ala-Ser-Gly-Lys-Pro-Val-Asn-His-Ser (SEQ ID NO 11), where any amide bond (—C(=O)—NH—) may be replaced by an amide isostere selected from the group consisting of:
—CH$_2$—NH—,
—CH$_2$—S—,
—CH$_2$—S(O)$_n$—, where n is 1 or 2,
—CH$_2$—CH$_2$—,
—CH=CH— (E or Z),
—C(=O)—CH$_2$—,
—CH(CN)—NH—,
—C(OH)—CH$_2$—, and
—O—C(=O)—NH—;

EF$_{bds}$ is selected from the group consisting of:
Asp-Trp-Ile-Glu-Gly-Glu-Thr (SEQ ID NO 12);
Arg-Asp-Trp-Ile-Glu-Gly-Glu-Thr (SEQ ID NO 13); and
Thr-Arg-Asp-Trp-Ile-Glu-Gly-Glu-Thr (SEQ ID NO 14), where any amide bond (—C(=O)—NH—) may be replaced by an amide isostere selected from the group consisting of:
—CH$_2$—NH—,
—CH$_2$—S—,
—CH$_2$—S(O)$_n$—, where n is 1 or 2,
—CH$_2$—CH$_2$—,
—CH=CH— (E or Z),
—C(=O)—CH$_2$—,
—CH(CN)—NH—,
—C(OH)—CH$_2$—, and
—O—C(=O)—NH—;

FG is Arg-Ala-Leu-Met (SEQ ID NO 15), where any amide bond (—C(=O)—NH—) may be replaced by an amide isostere selected from the group consisting of:
—CH$_2$—NH—,
—CH$_2$—S—,
—CH$_2$—S(O)$_n$—, where n is 1 or 2,
—CH$_2$—CH$_2$—,
—CH=CH— (E or Z),
—C(=O)—CH$_2$—,
—CH(CN)—NH—,
—C(OH)—CH$_2$—, and
—O—C(=O)—NH—;

a1 is a bond or is any amino acid sequence from one to about 14 amino acids in length, and a2 is a bond or is any amino acid sequence from one to about 14 amino acids in length, where any amide bond (—C(=O)—NH—) in a1 or a2 may be replaced by an amide isostere selected from the group consisting of:
—CH$_2$—NH—,
—CH$_2$—S—,
—CH$_2$—S(O)$_n$—, where n is 1 or 2,
—CH$_2$—CH$_2$—,
—CH=CH— (E or Z),
—C(=O)—CH$_2$—,
—CH(CN)—NH—,
—C(OH)—CH$_2$—, and
—O—C(=O)—NH—, provided that AA is from about 4 to about 20 amino acids in length;

R$_1$ is selected from
(a) hydroxy,
(b) C$_1$–C$_8$ alkoxy,
(c) C$_3$–C$_{12}$ alkenoxy,
(d) C$_6$–C$_{12}$ arlyoxy,
(e) acylamino-C$_1$–C$_8$-alkoxy
(f) pivaloyloxyethoxy,
(g) C$_6$–Cl$_{12}$ aryl-C$_1$–C$_8$-alkoxy where the aryl group is unsubstituted or substituted with one or more of the groups nitro, halo, C$_1$–C$_4$-alkoxy, and amino;

(h) hydroxy substituted $C_2$–$C_8$ substituted alkoxy; and
(i) dihydroxy substituted $C_3$–$C_8$ alkoxy;

$R_2$, $R_3$, $R_5$, $R_7$, $R_8$ are the same or different and are selected from (a) hydrogen,
(b) $C_6$–$C_{12}$ aryl where the aryl group is unsubstituted or substituted by one or more of the groups nitro, hydroxy, halo, $C_1$–$C_8$ alkyl, halo-$C_1$–$C_8$ alkyl, $C_1$–$C_8$ alkoxy, amino, phenyl, acetamido, benzamido, di-$C_1$–$C_8$ alkylamino, $C_6$–$C_{12}$ aroyl, $C_1$–$C_8$ alkanoyl, and hydroxy substituted $C_1$–$C_8$ alkyl,
(c) $C_1$–$C_{12}$ alkyl or alkenyl; $C_3$–$C_{10}$ cycloalkyl or $C_3$–$C_{12}$ substituted with any of halo, $C_1$–$C_8$ alkoxy, $C_6$–$C_{12}$ aryloxy, hydroxy, amino, acetamido, $C_1$–$C_8$ alkylamino, carboxy or carboxamide;

$R_2$ and $R_3$, $R_5$ and $R_6$, or $R_7$ and $R_8$ may optionally and independently be joined together to form a carbocyclic or heterocyclic ring of from four to seven atoms where the heteroatoms are selected from O, S, or $NR_{10}$ where $R_{10}$ is selected from hydrogen, $C_1$–$C_8$-alkyl, $C_2$–$C_8$-alkenyl, $C_6$–$C_{12}$-aryl, $C_3$–$C_{10}$ cycloalkyl, $C_6$–$C_{12}$-aryl-$C_1$–$C_8$-alkyl, $C_1$–$C_8$-alkanoyl, and $C_6$–$C_{12}$ aroyl, $R_4$ is selected from hydrogen, $C_1$–$C_8$-alkyl, $C_2$–$C_8$-alkenyl, $C_6$–$C_{12}$-aryl, $C_3$–$C_{10}$ cycloalkyl, $C_6$–$C_{12}$-aryl-$C_1$–$C_8$-alkyl, $C_1$–$C_8$-alkanoyl, and $C_6$–$C_{12}$ aroyl;

$R_2$ or $R_3$ may be optionally joined with $R_4$ to form a piperidine, pyrrolidine or thiazolidine ring;

X is selected from an O or S atom;

$NR_9$ wherein $R_9$ is hydrogen, $C_1$–$C_8$-alkyl, $C_3$–$C_8$-alkenyl, $C_3$–$C_{10}$ cycloalkyl, $C_6$–$C_{12}$-aryl, $C_6$–$C_{12}$-aryl-$C_1$–$C_8$-alkyl, $C_1$–$C_8$-alkanoyl,
or $C_6$–$C_{12}$ aroyl;
$C_6$–$C_{12}$ aryl;
$C_1$–$C_8$ alkanoyl; and
$(CH_2)k$ where k is an integer from 0 to 5; and pharmaceutically acceptable salts thereof.

As used herein and unless specified otherwise: alkyl and alkenyl denote straight or branched, saturated or unsaturated hydrocarbon chains , respectively; $C_6$–$C_{12}$ aryl groups denote unsubstituted aromatic rings or fused aromatic rings such as, for example, phenyl or naphthyl; halo denotes F, Cl, Br, or I atoms; alkoxy denotes an alkyl group bonded through O to the indicated site. Examples of $C_1$–$C_8$ alkyl or $C_2$–$C_8$ alkenyl groups include methyl, ethyl, propyl, isopropyl, butyl, t-butyl, pentyl, isopentyl, hexyl, vinyl, allyl, butenyl and the like; examples of $C_3$–$C_{10}$-cycloalkyl groups include cyclopropyl, cyclopentyl, cyclohexyl, and the like; heterocyclic rings include but are not limited to pyridyl, thienyl, furyl, indolyl, benzthienyl, imidazolyl, thiazolyl, quinolinyl and isoquinolinyl. The term "$C_1$–$C_8$ alkanoyl" encompasses groups such as formyl, acetyl, propionyl, butyryl, isobutyryl, valeryl, isovaleryl, pivaloyl, caproyl, and the like.

Further embodiments of the invention include amino acid variants of the IgE peptide antagonists described above. Such peptide variants have at least one amino acid residue in the peptide removed and a different residue inserted in its place. The sites of greatest interest for substitutional mutagenesis include the IgE binding determinant site(s) within any given IgE peptide antagonist. These sites are substituted in a relatively conservative manner by maintaining the structure of the peptide backbone in the area of substitution, maintaining the charge or hydrophobicity of the molecule at the target site, or maintaining side chain bulk at the target site. Such conservative substitutions are shown under the heading of preferred substitutions in Table 1 below.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Naturally occurring residues are divided into groups based on common side chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Any cysteine residues not involved in maintaining the proper conformation of the IgE peptide antagonist may be substituted, generally with serine, to improve the oxidative stability of the molecule.

Also encompassed within the scope of the invention are peptidomimetics of the IgE peptide antagonists described herein. Such peptidomimetics include peptides wherein at least one amino acid residue is substituted with an amino acid residue that is not commonly found in nature, such as the D isomer of the amino acid or an N-alkylated species of the amino acid. In other embodiments, peptidomimetics are constructed by replacing at least one amide bond ($—C(=O)—NH—$) in an IgE peptide antagonist with an amide isostere. Suitable amide isosteres include $—CH_2—NH—$, $—CH_2—S—$, $—CH_2—S(O)_n—$ (where n is 1 or 2), $—CH_2—CH_2—$, $—CH=CH—$ (E or Z), $—C(=O)—CH_2—$, $—CH(CN)—NH—$, $—C(OH)—CH_2—$, and $—O—C(=O)—NH—$. The amide bonds in an IgE peptide antagonist that are suitable candidates for replacement with amide isosteres include bonds that are hydrolyzable by the endogenous esterases or proteases of the intended subject of IgE peptide antagonist treatment.

The invention further provides for conjugates of any IgE peptide antagonist and additional chemical structures that support the intended function or functions of the particular IgE peptide antagonist. These conjugates include IgE peptide antagonist covalently bound to a macromolecule such as any insoluble, solid support matrix used in the diagnostic, screening or purification procedures discussed in Section V below. Suitable matrix materials include any substance that is chemically inert, has high porosity and has large numbers of functional groups capable of forming covalent linkages with peptide ligands. Examples of matrix materials and procedures for preparation of matrix-ligand conjugates are described in Dean et al. (eds) *Affinity Chromatography: A Practical Approach*, IRL Press (1985); Lowe, "An Introduction to Affinity Chromatography", in Work et al. (eds) *Laboratory Techniques in Biochemistry and Molecular Biology*, Vol. 7, Part II, North-Holland (1979); Porath et al., "Biospecific Affinity Chromatography", in Neurath et al. (eds), *The Proteins*, 3rd ed., Vol. 1, pp. 95–178 (1975); and Schott, *Affinity Chromatography*, Dekker (1984).

Also provided herein are conjugates of IgE peptide antagonist and any reporter moiety used in the diagnostic procedures discussed in Section V below. Such reporter moieties include moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to peptides. For instance, coupling agents such as dialdehydes, carbodiimides, dimaleimides, bis-imidates, bis-diazotized benzidine, and the like may be used to tag the IgE peptide antagonists with the above-described fluorescent, chemiluminescent, and enzyme labels. See, for example, U.S. Pat. Nos. 3,940,475 (fluorimetry) and 3,645,090 (enzymes); Hunter et al., *Nature*, 144: 945 (1962); David et al., *Biochemistry*, 13: 1014–1021 (1974); Pain et al., *J. Immunol. Methods*, 40: 219–230 (1981); and Nygren, *J. Histochem. and Cytochem.*, 30: 407–412 (1982). Preferred labels herein are enzymes such as horseradish peroxidase and alkaline phosphatase.

Further provided herein are conjugates of IgE peptide antagonist and any immunogen used in the production of anti-IgE antibodies described in section V below. Suitable immunogens include any protein that is immunogenic in the species to be immunized. The IgE peptide antagonist can be covalently bound to the immunogen with a bifunctional cross-linking reagent. Alternatively, the IgE peptide antagonist/immunogen conjugate can be produced as a fusion protein in a recombinant expression system according to the procedures described in Section II below.

II. Methods of Making IgE Peptide Antagonists
1. Chemical Synthesis
a. General Procedures One method of producing IgE peptide antagonists involves chemical synthesis of the polypeptide, followed by treatment under oxidizing conditions appropriate to obtain the native conformation, that is, the correct disulfide bond linkages. This can be accomplished using methodologies well known to those skilled in the art (see Kelley, R. F. & Winkler, M. E. in *Genetic Engineering Principles and Methods*, Setlow, J. K., ed., Plenum Press, N.Y., vol. 12, pp 1–19 (1990); Stewart, J. M. & Young, J. D. *Solid Phase Peptide Synthesis* Pierce Chemical Co. Rockford, Ill. (1984); see also U.S. Pat. Nos. 4,105,603; 3,972,859; 3,842,067; and 3,862,925).

Polypeptides of the invention may be conveniently prepared using solid phase peptide synthesis (Merrifield, *J. Am. Chem. Soc.*, 85:2149 (1964); Houghten, *Proc. Natl. Acal. Sci. USA* 82:5132 (1985)). Solid phase synthesis begins at the carboxy-terminus of the putative peptide by coupling a protected amino acid to a suitable resin (e.g. chloromethylated polystyrene resin) as shown in FIGS. 1-1 and 1-2, on pages 2 and 4 of Stewart and Young supra. After removal of the α-amino protecting group with, for example, trifluoroacetic acid (TFA) in methylene chloride and neutralizing in, for example TEA, the next α-amino- and sidechain protected amino acid in the synthesis is added. The remaining α-amino- and, if necessary, side-chain-protected amino acids are then coupled sequentially in the desired order by condensation to obtain an intermediate compound connected to the resin. Alternatively, some amino acids may be coupled to one another forming a peptide prior to addition of the peptide to the growing solid phase polypeptide chain.

The condensation between two amino acids, or an amino acid and a peptide, or a peptide and a peptide can be carried out according to the usual condensation methods such as the azide method, mixed acid anhydride method, DCC (N,N'-dicyclohexylcarbodiimide) or DIC (N,N'-diisopropylcarbodiimide)methods, active ester method (p-nitrophenyl ester method, BOP (benzotriazole-1-yl-oxy-tris (dimethylamino) phosphonium hexafluorophosphate) method, N-hydroxysuccinic acid imido ester method, etc, and Woodward reagent K method.

Common to chemical syntheses of peptides is the protection of any reactive side-chain groups of the amino acids with suitable protecting groups. Ultimately these protecting groups are removed after the desired polypeptide chain has been sequentially assembled. Also common is the protection of the α-amino group on an amino acid or a fragment while that entity reacts at the carboxyl group followed by the selective removal of the α-amino-protecting group to allow subsequent reaction to take place at that location. Accordingly, it is common in polypeptide synthesis that an intermediate compound is produced which contains each of the amino acid residues located in the desired sequence in the peptide chain with various of these residues having side-chain protecting groups attached. These protecting groups are then commonly removed substantially at the same time so as to produce the desired resultant product following removal from the resin.

Suitable protective groups for protecting the α- and ε-amino side chain groups are exemplified by benzyloxycarbonyl (abbreviated Z), isonicotinyloxycarbonyl (iNOC), O-chlorobenzyloxycarbonyl (Z(2Cl)), p-nitrobenzyloxycarbonyl (Z($NO_2$)), p-methoxybenzyloxycarbonyl (Z(OMe)), t-butoxycarbonyl, (Boc), t-amyloxycarbonyl (Aoc), isoborrnyloxycarbonyl, adamatyloxycarbonyl, 2-(4-biphenyl)-2-propyloxycarbonyl (Bpoc), 9-fluorenylmethoxycarbonyl (Fmoc), methylsulfonyiethoxycarbonyl (Msc), trifluoroacetyl, phthalyl, formyl, 2-nitrophenylsulphenyl (NPS), diphenylphosphinothioyl (Ppt), dimethylophosphinothioyl (Mpt) and the like.

Protective groups for the carboxy functional group are exemplified by; benzyl ester (OBzl), cyclohexyl ester (Chx), 4-nitrobenzyl ester (ONb), t-butyl ester (Obut), 4-pyridylmethyl ester (OPic), and the like. It is often desirable that specific amino acids such as arginine, cysteine, and serine possessing a functional group other than amino and carboxyl groups are protected by a suitable protective group. For example, the guanidino group of arginine may be protected with nitro, p-toluenesulfonyl, benzyloxycarbonyl, adamantyloxycarbonyl, p-methoxybenzenesulfonyl, 4-methoxy-2, 6-dimethylbenzenesulfonyl (Mds), 1,3,5-trimethylphenysulfonyl (Mts), and the like. The thiol group of cysteine may be protected with p-methoxybenzyl, triphenylmethyl, acetylaminomethyl ethylcarbamoyle, 4-methylbenzyl, 2, 4, 6-trimethy-benzyl (Tmb) etc, and the hydroxyl group of serine can be protected with benzyl, t-butyl, acetyl, tetrahydropyranyl and the like.

Stewart and Young supra provides detailed information regarding procedures for preparing peptides. Protection of α-amino groups is described on pages 14–18, and side-chain blockage is described on pages 18–28. A table of protecting groups for amine, hydroxyl and sulfhydryl functions is provided on pages 149–151.

After the desired amino acid sequence has been completed, the intermediate peptide is removed from the resin support by treatment with a reagent, such as liquid HF and one or more thio-containing scavengers, which not only cleaves the peptide from the resin, but also cleaves all the remaining side-chain protecting groups. Following HF cleavage, the protein sequence is washed with ether, transferred to a large volume of dilute acetic acid, and stirred at pH adjusted to about 8.0 with ammonium hydroxide.

Preferably in order to avoid alkylation of residues in the polypeptide, (for example, alkylation of methionine, cysteine, and tyrosine residues) a thio-cresol and cresol scavenger mixture is used. The resin is washed with ether, and immediately transferred to a large volume of dilute acetic acid to solubilize and minimize intermolecular cross-linking. A 250 $\mu$M polypeptide concentration is diluted in about 2 liters of 0.1 M acetic acid solution. The solution is then stirred and its pH adjusted to about 8.0 using ammonium hydroxide. Upon pH adjustment, the polypeptide takes its desired conformational arrangement.

b. Non-peptide Linkages

In one embodiment of the invention, the amide linkages (—C(=O)—NH—) are replaced with amide isostere linkages such as; —CH$_2$—NH—, —CH$_2$—S—, —CH$_2$—CH$_2$—, —CH=CH— (cis and trans), —C(=O)—CH$_2$—, —CH(OH)—CH$_2$—, —CH(CN)—NH—, —O—C(=O)—NH— and —CH$_2$—SO—, by methods known in the art. The following references describe preparation of peptide analogs which include these alternative-linking moieties: Spatola, A. F., Vega Data 1(3): "Peptide Backbone Modifications" (General Review) (March 1983), Spatola, A. F., in "Chemistry and Biochemistry of Amino Acids Peptides and Proteins", B. Weinstein, ed., Marcel Dekker, New York, P. 267 (1983); Morley, J. S., *Trends Pharm. Sci.* pp. 463–468; Hudson, D. et al. *Int. J. Pept. Prot. Res.* 14:177–185 (1979) (—CH$_2$NH—, —CH$_2$CH$_2$—); Spatola, A. F., et al., *Life Sci.* 38:1243–1249 (1986) (—CH$_2$—S—); Hann, M. M., *J. Chem. Soc. Perkin. Trans. I* 307–314 (1982) (—CH=CH—, cis and trans); Almquist, R. G., et al., *J. Med. Chem.* 23:1392–1398 (1980) (—C(=O)—CH$_2$—); Jennings-White C., et al., *Tetrahedron Lett* 23:(1982) (—C(=O)—CH$_2$—); Szelke, M., et al., EP Application No. 45665 (1982) *Chem Abs* 97:39405 (1982) (—CH(OH)—CH$_2$); Holladay, M. W., et al., *Tetrahedron Lett* 24:4401–4404 (1983) (—C(OH)—CH$_2$—); Hruby, V. J. *Life Sci* 31:189–199 (1982) (—CH$_2$S—); and Cho, C.Y. et al, *Science* 261:1303–1305 (1993) (—O—C(=O)—NH—).

2. Recombinant Synthesis a. Construction of IgE Peptide Antagonist-Encoding DNA

DNA encoding the desired IgE peptide antagonist can be prepared by a variety of methods known in the art. These methods include, but are not limited to, chemical synthesis by any of the methods described in Engels et al., *Agnew. Chem. Int. Ed. Engl.*, 28: 716–734 (1989), the entire disclosure of which is incorporated herein by reference, such as the triester, phosphite, phosphoramidite and H-phosphonate methods. In one embodiment, codons preferred by the expression host cell are used in the design of the IgE peptide antagonist DNA.

A variation on the above procedures contemplates the use of gene fusions, wherein the gene encoding IgE peptide antagonist is associated, in the vector, with a gene encoding another protein or a fragment of another protein. This results in IgE peptide antagonist being produced by the host cell as a fusion with another protein. The "other" protein is often a protein or peptide which can be secreted by the cell, making it possible to isolate and purify the desired protein from the culture medium and eliminating the necessity of destroying the host cells which arises when the desired protein remains inside the cell. Alternatively, the fusion protein can be expressed intracellularly. It is useful to use fusion proteins that are highly expressed.

The use of gene fusions, though not essential, can facilitate the expression of heterologous proteins in *E. coli* as well as the subsequent purification of those gene products (Harris, T. J. R. in *Genetic Engineering*, Williamson, R., Ed., Academic, London, Vol. 4, p. 127(1983); Uhlen, M. & Moks, T., *Methods Enzymol.* 185:129–143 (1990)). Protein A fusions are often used because the binding of protein A, or more specifically the Z domain of protein A, to IgG provides an "affinity handle" for the purification of the fused protein (Nilsson, B. & Abrahmsen, L. *Methods Enzymol.* 185:144–161 (1990)). It has also been shown that many heterologous proteins are degraded when expressed directly in *E. coli*, but are stable when expressed as fusion proteins (Marston, F. A. O., *Biochem J.* 240: 1 (1986)).

Fusion proteins can be cleaved using chemicals, such as cyanogen bromide, which cleaves at a methionine, or hydroxylamine, which cleaves between an Asn and Gly. Using standard recombinant DNA methodology, the nucleotide base pairs encoding these amino acids may be inserted just prior to the 5' end of the IgE peptide antagonist gene.

Alternatively, one can employ proteolytic cleavage of fusion proteins, which has been recently reviewed (Carter, P. (1990) in *Protein Purification: From Molecular Mechanisms to Large-Scale Processes*, Ladisch, M. R., Willson, R. C., Painton, C. C., and Builder, S. E., eds., American Chemical Society Symposium Series No. 427, Ch 13, 181–193).

Proteases such Factor Xa, thrombin, subtilisin and mutants thereof, have been successfully used to cleave fusion proteins. Typically, a peptide linker that is amenable to cleavage by the protease used is inserted between the "other" protein (e.g., the Z domain of protein A) and the protein of interest, such as ANF or an ANF variant. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

Various techniques are also available which may now be employed to produce mutant IgE peptide antagonists, which encodes for additions, deletions, or changes in amino acid sequence of the resultant protein relative to the parent IgE peptide antagonist molecule.

By way of illustration, with expression vectors encoding IgE peptide antagonist in hand, site specific mutagenesis (Kunkel et al., *Methods Enzymol.* 204:125–139 (1991); Carter, P., et al., *Nucl. Acids. Res.* 13:4331 (1986); Zoller, M. J. et al., *Nucl. Acids Res.* 10:6487 (1982)), cassette mutagenesis (Wells, J. A., et al., *Gene* 34:315 (1985)), restriction selection mutagenesis (Wells, J. A., et al., *Philos. Trans, R. Soc. London SerA* 317, 415 (1986)) or other known techniques may be performed on the IgE peptide antagonist DNA. The mutant DNA can then be used in place of the parent DNA by insertion into the aforementioned expression vectors. Growth of host bacteria containing the expression vectors with the mutant DNA allows the production of mutant IgE peptide antagonist, which can be isolated as described herein.

b. Insertion of DNA into a Cloning Vehicle

The DNA encoding IgE peptide antagonist is inserted into a replicable vector for further cloning (amplification of the DNA) or for expression. Many vectors are available, and selection of the appropriate vector will depend on (1) whether it is to be used for DNA amplification or for DNA expression, (2) the size of the DNA to be inserted into the vector, and (3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence.

(i) Signal Sequence Component

In general, a signal sequence may be a component of the vector, or it may be a part of the IgE peptide antagonist DNA that is inserted into the vector.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the $2\mu$ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is homologous to a sequence found in Bacillus genomic DNA. Transfection of Bacillus with this vector results in homologous recombination with the genome and insertion of the IgE peptide antagonist DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g. the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., *J. Molec. Appl. Genet.*, 1: 327 (1982)), mycophenolic acid (Mulligan et al., *Science,* 209: 1422 (1980)) or hygromycin (Sugden et al., *Mol. Cell. Biol.,* 5: 410–413 (1985)). The three examples given above employ bacterial genes under eukaryotic control to convey resistance to the appropriate drug (G418 or neomycin (geneticin), xgpt (mycophenolic acid), and hygromycin, respectively.)

Another example of suitable selectable markers for mammalian cells are those that enable the identification of cells competent to take up the IgE peptide antagonist nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the IgE peptide antagonist. Amplification is the process by which genes in greater demand for the production of a protein critical for growth are reiterated in tandem within the chromosomes of successive generations of recombinant cells. Increased quantities of the IgE peptide antagonist are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA,* 77: 4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the IgE peptide antagonist. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding the IgE peptide antagonist, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7. Stinchcomb et al., *Nature,* 282: 39 (1979); Kingsman et al., *Gene,* 7: 141 (1979); or Tschemper et al., *Gene,* 10: 157 (1980). The trp1 gene provides a selection marker for a mutant strain of yeast lacking the ability to grow in tryptophan, for example, ATCC No. 44076 or PEP4-1. Jones, *Genetics,* 85: 12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

(iv) Promoter Component

Expression vectors usually contain a promoter that is recognized by the host organism and is operably linked to the IgE peptide antagonist nucleic acid. Promoters are untranslated sequences located upstream (5') to the start codon of a structural gene (generally within about 100 to 1000 bp) that control the transcription and translation of a particular nucleic acid sequence, such as the IgE peptide antagonist, to which they are operably linked. Such promoters typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known.

Promoters suitable for use with prokaryotic hosts include the β-lactamase and lactose promoter systems (Chang et al., *Nature,* 275: 615 (1978); and Goeddel et al., *Nature,* 281: 544 (1979)), alkaline phosphatase, a tryptophan (trp) promoter system (Goeddel, *Nucleic Acids Res.,* 8: 4057 (1980) and EP 36,776) and hybrid promoters such as the tac promoter (deBoer et al., *Proc. Natl. Acad. Sci. USA,* 80: 21–25 (1983)). However, other known bacterial promoters are suitable. Their nucleotide sequences have been published, thereby enabling a skilled worker to operably ligate them to DNA encoding the IgE peptide antagonist (Siebenlist et al., *Cell,* 20: 269 (1980)) using linkers or adaptors to supply any required restriction sites. Promoters for use in bacterial systems also generally will contain a Shine-Dalgarno (S.D.) sequence operably linked to the DNA encoding the IgE peptide antagonist.

Suitable promoting sequences for use with yeast hosts include the promoters for 3-phosphoglycerate kinase (Hitzeman et al., *J. Biol. Chem.,* 255: 2073 (1980)) or other glycolytic enzymes (Hess et al., *J. Adv. Enzyme Reg.,* 7: 149 (1968); and Holland, *Biochemistry,* 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

IgE peptide antagonist transcription from vectors in mammalian host cells is controlled by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, and from heat-shock promoters, provided such promoters are compatible with the host cell systems.

The early and late promoters of the SV40 virus are conveniently obtained as an SV40 restriction fragment that also contains the SV40 viral origin of replication. Fiers et al., *Nature,* 273: 113 (1978); Mulligan and Berg, *Science,* 209: 1422–1427 (1980); Pavlakis et al., *Proc. Natl. Acad. Sci. USA,* 78: 7398–7402 (1981). The immediate early promoter of the human cytomegalovirus is conveniently obtained as a HindIII E restriction fragment. Greenaway et al., *Gene,* 18: 355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature,* 295: 503–508 (1982) on expressing cDNA encoding immune interferon in monkey cells, Reyes et al., *Nature,* 297: 598–601 (1982) on expression of human β-interferon cDNA in mouse cells under the control of a thymidine kinase promoter from herpes simplex virus, Canaani and Berg, *Proc. Natl. Acad. Sci. USA,* 79: 5166–5170 (1982) on expression of the human interferon β1 gene in cultured mouse and rabbit cells, and Gorman et al., *Proc. Natl. Acad. Sci. USA,* 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding IgE peptide antagonist by higher eukaryotes is often increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins et al., *Proc. Natl. Acad. Sci. USA,* 78: 993 (1981)) and 3' (Lusky et al., *Mol. Cell Bio.,* 3: 1108 (1983)) to the transcription unit, within an intron (Banerji et al., *Cell,* 33: 729 (1983)) as well as within the coding sequence itself (Osborne et al., *Mol. Cell Bio.,* 4: 1293 (1984)). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature,* 297: 17–18 (1982) on enhancing elements for activation of eukaryotic promoters. The enhancer may be spliced into the vector at a position 5' or 3' to the IgE peptide antagonist DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the IgE peptide antagonist. The 3' untranslated regions also include transcription termination sites.

Suitable vectors containing one or more of the above listed components and the desired coding and control sequences are constructed by standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.,* 9: 309 (1981) or by the method of Maxam et al., *Methods in Enzymology,* 65: 499 (1980).

Particularly useful in the practice of this invention are expression vectors that provide for the transient expression in mammalian cells of DNA encoding the IgE peptide antagonist. In general, transient expression involves the use of an expression vector that is able to replicate efficiently in a host cell, such that the host cell accumulates many copies of the expression vector and, in turn, synthesizes high levels of a desired polypeptide encoded by the expression vector.

Other methods, vectors, and host cells suitable for adaptation to the synthesis of the IgE peptide antagonist in recombinant vertebrate cell culture are described in Gething et al., *Nature,* 293: 620–625 (1981); Mantei et al., *Nature,* 281: 40–46 (1979); Levinson et al., EP 117,060; and EP 117,058. A particularly useful plasmid for mammalian cell culture expressior of the IgE peptide antagonist is pRK5 (EP pub. no. 307,247) or pSVI6B (PCT pub. no. WO 91/08291 published Jun. 13, 1991).

c. Selection and Transformation of Host Cells

Suitable host cells for cloning or expressing the vectors herein are the prokaryote, yeast, or higher eukaryote cells described above. Suitable prokaryotes include eubacteria, such as Gram-negative or Gram-positive organisms, for example, *E. coli*, Bacilli such as *B. subtilis*, Pseudomonas species such as *P. aeruginosa, Salmonella typhimurium,* or *Serratia marcescens.* One preferred *E. coli* cloning host is *E. coli* 294 (ATCC 31,446), although other strains such as *E. coli* B, *E. coli* χ1776 (ATCC 31,537), and *E. coli* W3110 (ATCC 27,325) are suitable. These examples are illustrative rather than limiting. Preferably the host cell should secrete minimal amounts of proteolytic enzymes. Alternatively, in vitro methods of cloning, e.g. PCR or other nucleic acid polymerase reactions, are suitable.

In addition to prokaryotes, eukaryotic microbes such as filamentous fungi or yeast are suitable hosts for vectors containing IgE peptide antagonist DNA. *Saccharomyces cerevisiae,* or common baker's yeast, is the most commonly used among lower eukaryotic host microorganisms. However, a number of other genera, species, and strains are commonly available and useful herein, such as *S. pombe* (Beach and Nurse, *Nature,* 290: 140 (1981)), *Kluyveromyces lactis* (Louvencourt et al., *J. Bacteriol.,* 737 (1983)), yarrowia (EP 402,226), Pichia pastoris (EP 183,070), *Trichoderma reesia* (EP 244,234), *Neurospora crassa* (Case et al., *Proc. Natl. Acad. Sci. USA,* 76: 5259–5263 (1979)), and Aspergillus hosts such as *A. nidulans* (Ballance et al., *Biochem. Biophys. Res. Commun.,* 112: 284–289 (1983); Tilburn et al., *Gene,* 26: 205–221 (1983); Yelton et al., *Proc. Natl. Acad. Sci. USA,* 81: 1470–1474 (1984)) and *A. niger* (Kelly and Hynes, *EMBO J.,* 4: 475–479 (1985)).

Host cells derived from multicellular organisms can also be used in the recombinant production of IgE peptide antagonist. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified. See, e.g., Luckow et al., *Bio/Technology,* 6: 47–55 (1988); Miller et al., in *Genetic Engineering,* Setlow, J. K. et al., 8: 277–279 (Plenum Publishing, 1986), and Maeda et al., *Nature,* 315: 592–594 (1985). A variety of such viral strains are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens,* which has been previously manipulated to contain the IgE peptide antagonist DNA. During incubation of the plant cell culture with *A. tumefaciens*; the DNA encoding IgE peptide antagonist is transferred to the plant cell host such that it is transfected, and will, under appropriate conditions, express the IgE peptide antagonist DNA. In addition, regulatory and signal sequences compatible with plant cells are available, such as the nopaline synthase promoter and polyadenylation signal sequences. Depicker et al., *J. Mol. Appl. Gen.,* 1: 561 (1982). In addition, DNA segments isolated from the upstream region of the T-DNA 780 gene are capable of activating or increasing transcription levels of plant-expressible genes in recombinant DNA-containing plant tissue. See EP 321,196 published Jun. 21, 1989.

However, interest has been greatest in vertebrate cells, and propagation of vertebrate cells in culture (tissue culture) has become a routine procedure in recent years (*Tissue Culture,* Academic Press, Kruse and Patterson, editors (1973)). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.,* 36: 59 (1977)); baby hamster kidney cells (BHK, ATCC CCL 10); Chinese hamster ovary cells/-DHFR (CHO, Urlaub and Chasin, *Proc. Natl. Acad. Sci. USA,* 77: 4216 (1980)); mouse sertoli cells (TM4, Mather, *Biol. Reprod.,* 23: 243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383: 44–68 (1982)); MRC 5 cells; FS4 cells; and a human hepatoma cell line (Hep G2). Preferred host cells are human embryonic kidney 293 and Chinese hamster ovary cells.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., *Gene,* 23: 315 (1983) and WO 89/05859 published Jun. 29, 1989. For mammalian cells without such cell walls, the calcium phosphate precipitation method described in sections 16.30–16.37 of Sambrook et al., supra, is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.,* 130: 946 (1977) and Hsiao et al., *Proc. Natl. Acad. Sci. (USA),* 76: 3829 (1979). However, other methods for introducing DNA into cells such as by nuclear injection, electroporation, or by protoplast fusion may also be used.

d. Culturing the Host Cells

Prokaryotic cells used to produce the IgE peptide antagonist are cultured in suitable media as described generally in Sambrook et al., supra.

The mammalian host cells used to produce the IgE peptide antagonist can be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham and Wallace, *Meth. Enz.,* 58: 44 (1979), Barnes and Sato, *Anal. Biochem.,* 102: 255 (1980), U.S. Pat. Nos. 4,767,704; 4,657,866; 4,927,762; or 4,560,655; WO 90/03430; WO 87/00195; U.S. Pat. Re. No. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

e. Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA,* 77: 5201–5205 (1980)), dot blotting (DNA analysis), or in situ hybridization, using an appropriately labeled probe, based on the sequences provided herein. Various labels may be employed, most commonly radioisotopes, particularly $^{32}p$ However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product, where the labels are usually visually detectable, such as enzymatic labels, fluorescent labels, luminescent labels, and the like. A particularly sensitive staining technique suitable for use in the present invention is described by Hsu et al., *Am. J. Clin. Path.,* 75: 734–738 (1980).

Antibodies useful for immunohistochemical staining and/or assay of sample fluids may be either monoclonal or polyclonal, and may be prepared in any mammal. Conveniently, the antibodies can be prepared against an IgE peptide antagonist as described in Section V below.

f. Purification of the IgE Peptide Antagonist

The IgE peptide antagonist is recovered from the culture cells by solubilizing cell membrane in detergent. As a first step, the cells are centrifuged to separate them from culture medium. The membrane and soluble protein fractions are then separated. The IgE peptide antagonist may then be purified from the membrane fraction of the culture lysate by solubilization with detergents followed by suitable purification procedures: fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins and ligand affinity using the appropriate anti-IgE antibody or $Fc_{\epsilon}RI$ ligand-binding domain immobilized on a matrix.

If a conformationally restrained structure is desired, the IgE peptide antagonist can be cyclized or cross-linked. Known cyclization procedures such as those described in PCT 90/01331 or Lys/Asp cyclization using Nα-Boc-amino acids on solid-phase support with Fmoc/9-fluorenylmethyl (Ofm) side-chain protection for Lys/Asp, followed by piperidine treatment and cyclization, are useful. Methods which depend upon cross-linking or cyclization through residue side chains may require that an extraneous residue be inserted at the C and/or N terminus of the IgE peptide antagonist to provide a suitable cyclizing or cross-linking site.

Glu and Lys side chains also have been crosslinked in preparing cyclic or bicyclic peptides: the peptide is synthesized by solid phase chemistry on a p-methylbenzhydrylamine resin, the peptide is cleaved from the resin and deprotected. The cyclic peptide is formed using diphenylyphosphorylazide in diluted methylformamide. For an alternative procedure, see Schiller et al., *Peptide Protein Res.* 25:171–77 (1985). See also U.S. Pat. No. 4,547,489.

Disulfide crosslinked or cyclized peptides are generated by conventional methods. The method of Pelton et al., *J. Med Chem.*, 29:2370–2375 (1986) is suitable. Also useful are thiomethylene bridges (*Tetrahedron Letters* 25:2067–2068 (1984). See also Cody et al., *J. Med Chem.*: 28:583 (1985).

Typically, extraneous residues which are to participate in cyclization or cross-linking are inserted at the N- and C-termini of the chosen sequence as part of the synthesis of the polypeptide precursor to be employed in the procedure. The desired cyclic or cross-linked peptides are purified by gel filtration followed by reversed-phase high pressure liquid chromatography or other conventional procedures. The peptides are sterilized by 0.2 $\mu$m filtration and formulated into conventional pharmacologically acceptable vehicles.

Following production, the IgE peptide antagonists can be screened for a desired activity. If $Fc_\epsilon RI$ binding is desired, the IgE peptide antagonist can assayed for the ability to bind $Fc_\epsilon RI$ $\alpha$-chain. Such $Fc_\epsilon RI$ $\alpha$-chain binding activity can be measured, for example, in an ELISA assay wherein microtiter plates are coated with $Fc_\epsilon RI$ $\alpha$-chain, coated plates are contacted with radiolabelled IgE peptide antagonist, washed free of unbound antagonist, and then the bottoms of the plates are cut out and autoradiographed. Alternatively, the IgE peptide antagonist can be assayed for the ability to bind $Fc_\epsilon RI$ $\alpha$-chain in a FACS assay wherein antagonist conjugated to a fluorescent label, such as fluorescein isothiocyanate (FITC) or phycoerythrin (PE), is contacted with transfected cells expressing $Fc_\epsilon RI$ $\alpha$-chain followed by flow cytometer analysis of the cell sample as described in Example 1 below.

If $IgE/Fc_\epsilon RI$ binding inhibition is desired, the IgE peptide antagonist can be assayed for such activity by contacting cells expressing $Fc_\epsilon RI$ $\alpha$-chain with fluorescent labelled IgE in the presence or absence of antagonist, followed by flow cytometer analysis of the cell samples as described in Example 1 below. Alternatively, the IgE peptide antagonist can be assayed for the ability to inhibit IgE-mediated histamine release in mast cells or basophils in any of the histamine release assays described in copending U.S. Ser. No. 08/165,436 filed Dec. 10, 1993, the entire disclosure of which is incorporated herein by reference.

III. IgE Variants

The IgE antagonists of the invention also include IgE variants that comprise one or more of the important binding determinants of IgE. Preferably, the IgE variant possesses at least about 35% homology to the corresponding sequence of the $Fc_\epsilon$ domain(s) of human IgE and the important binding determinant(s) are located in areas of the IgE variant analogous to the position(s) occupied by the determinant(s) in the $Fc_\epsilon 3$ domain of native IgE. Such IgE variants are designed by using the amino acid sequence of other human immunoglobulins, including IgG, IgA, IgD and IgM, or the amino acid sequence of IgE, IgG, IgA, IgD or IgM in any non-human species, such as mouse or rat, as a template, and inserting within or conjugating to the template amino acid sequence the amino acid sequence(s) of $CD_{bds}$, $EF_{bds}$, FG, or any combination thereof. In one embodiment, the IgE binding determinant amino acid sequence(s) is substituted for native amino acid sequence(s) in the template immunoglobulin. Preferably, the IgE binding determinant amino acid sequence(s) is substituted for the homologous amino acid sequence or sequence(s) in the template determined by the homology scan methodology described in B. C. Cunningham, P. Jhurani, P. Ng, J. A. Wells, *Science* 243, 1330 (1989). A template immunoglobulin amino acid sequence that is determined to be homologous (by the method of Cunningham et al.) to a given human IgE amino acid sequence is referred to herein as the "homologous" or "corresponding" sequence in the template immunoglobulin.

In a preferred embodiment of the invention, the IgE variant comprises all of the human IgE sequences that are critical for human $IgE/Fc_\epsilon RI$ binding, namely, the CD loop core amino acid sequence, the EF loop core amino acid sequence, and the FG loop. For example, the invention provides IgE variants comprising one amino acid sequence selected from the group consisting of $CD_{bds}$, one amino acid sequence selected from the group consisting of $EF_{bds}$, and the amino acid sequence Arg-Ala-Leu-Met (SEQ ID NO 15). In a particularly preferred embodiment, the $CD_{bds}$, $EF_{bds}$ and Arg-Ala-Leu-Met (SEQ ID NO 15) amino acid sequences are substituted for homologous sequences in the immunoglobulin template. Even more preferred are IgE variants wherein a $CD_{bds}$ amino acid sequence, an $EF_{bds}$ amino acid sequence and an Arg-Ala-Leu-Met (SEQ ID NO 15) amino acid sequence are contained in an $Fc_\epsilon 3$-homologous amino acid sequence that is at least 35% homologous to the corresponding amino acid sequence in the $Fc_\epsilon 3$ domain of human IgE.

In another preferred embodiment of the invention, the IgE variant comprises at least one amino acid sequence containing the entire CD, EF or FG loop of the human IgE $Fc_\epsilon 3$ domain. For example, the invention provides IgE variants comprising one or more amino acid sequences selected from the group consisting of amino acid residues 407–420 (SEQ ID NO 11), 445–453 (SEQ ID NO 14), and 465–469 (SEQ ID NO 15) of human IgE. In a particularly preferred embodiment, the IgE variant comprises amino acid residues 407–420 (SEQ ID NO 11), 445–453 (SEQ ID NO 14), and 465–469 (SEQ ID NO 15) of human IgE. Even more preferred are IgE variants wherein amino acid residues 407–420 (SEQ ID NO 11), 445–453 (SEQ ID NO 14), and 465–469 (SEQ ID NO 15) of human IgE are contained in an $Fc_\epsilon 3$-homologous amino acid sequence that is at least 35% homologous to the corresponding amino acid sequence in the $Fc_\epsilon 3$ domain of human IgE.

Alternatively, any region of the human IgE $Fc_\epsilon 3$ domain spanning one or more of the $CD_{bds}$, $EF_{bds}$ and FG determinants, or even the entire $Fc_\epsilon 3$ domain, can be inserted in, conjugated to or used to replace native amino acid sequence in the immunoglobulin template. In a preferred embodiment, such $Fc_\epsilon 3$ domain regions are substituted for a homologous region in the immunoglobulin template.

In a further embodiment, any of the above-described IgE variants can be modified to include amino acid residues 361–365 (SEQ ID NO 44) from the $Fc_\epsilon 2$–$Fc_\epsilon 3$ hinge region of human IgE, or the entire $Fc_\epsilon 2$–$Fc_\epsilon 3$ hinge region (amino acid residues 357–365) (SEQ ID NO 53). In a preferred embodiment, the $Fc_\epsilon 2$–$Fc_\epsilon 3$ hinge residues are substituted for the homologous amino acid residues in the immunoglobulin template.

In an additional, preferred embodiment of the invention, the IgE variant is derived from a human IgG1 template. For example, any of the IgE/IgG1 substitutions detailed in Table 2 below can be used to create an IgE antagonist from an IgG1 template.

TABLE 2

| IgE | | | IgG1 | |
|---|---|---|---|---|
| domain | binding determinant | import residues | domain | target residues |
| $Fc_\epsilon 3$ | $CD_{bds}$ | 408–415 | $Fc_{\gamma 1}2$ | 292–300 |
| $Fc_\epsilon 3$ | $CD_{bds}$ | 408–416 | $Fc_{\gamma 1}2$ | 292–301 |
| $Fc_\epsilon 3$ | $CD_{bds}$ | 408–417 | $Fc_{\gamma 1}2$ | 292–302 |
| $Fc_\epsilon 3$ | $CD_{bds}$ | 408–418 | $Fc_{\gamma 1}2$ | 292–303 |
| $Fc_\epsilon 3$ | $CD_{bds}$ | 408–419 | $Fc_{\gamma 1}2$ | 292–304 |
| $Fc_\epsilon 3$ | $CD_{bds}$ | 408–420 | $Fc_{\gamma 1}2$ | 292–305 |
| $Fc_\epsilon 3$ | $CD_{bds}$ | 407–415 | $Fc_{\gamma 1}2$ | 291–300 |
| $Fc_\epsilon 3$ | $CD_{bds}$ | 407–416 | $Fc_{\gamma 1}2$ | 291–301 |
| $Fc_\epsilon 3$ | $CD_{bds}$ | 407–417 | $Fc_{\gamma 1}2$ | 291–302 |
| $Fc_\epsilon 3$ | $CD_{bds}$ | 407–418 | $Fc_{\gamma 1}2$ | 291–303 |
| $Fc_\epsilon 3$ | $CD_{bds}$ | 407–419 | $Fc_{\gamma 1}2$ | 291–304 |
| $Fc_\epsilon 3$ | $CD_{bds}$ | 407–420 | $Fc_{\gamma 1}2$ | 291–305 |
| $Fc_\epsilon 3$ | $EF_{bds}$ | 447–453 | $Fc_{\gamma 1}2$ | 331–337 |
| $Fc_\epsilon 3$ | $EF_{bds}$ | 446–453 | $Fc_{\gamma 1}2$ | 330–337 |
| $Fc_\epsilon 3$ | $EF_{bds}$ | 445–453 | $Fc_{\gamma 1}2$ | 329–337 |
| $Fc_\epsilon 3$ | FG | 465–469 | $Fc_{\gamma 1}2$ | 349–352 |

The invention also provides for IgE variants constructed from a human IgG1 template wherein multiple IgE binding determinants are substituted for the homologous amino acid sequences in IgG1. IgE variants with the following combinations of IgE binding determinants can be constructed: one $CD_{bds}$ and one $EF_{bds}$; one $EF_{bds}$ and FG; one $CD_{bds}$ and FG; or one $CD_{bds}$, one $EF_{bds}$ and FG. In a preferred embodiment, amino acids 291–305 (SEQ ID NO 58), 329–337 (SEQ ID NO 59), and 349–352 (SEQ ID NO 35) in the $Fc_{\gamma 1}2$ domain of IgG1 are substituted by IgE residues 407–420 (SEQ ID NO 11), 445–453 (SEQ ID NO 14), and 465–469 (SEQ ID NO 15), respectively, as described in the construction of IgGEL in Example 2 below.

In another preferred embodiment, the IgG1 template contains, in addition to one or more IgE binding determinants, amino acid sequence containing residues 361–365 (SEQ ID NO 44) from the $Fc_\epsilon 2$–$Fc_\epsilon 3$ hinge region of IgE substituted for the homologous sequence in the $Fc_{\gamma 1}1$–$Fc_{\gamma 1}2$ hinge region of IgG1. In a particularly preferred embodiment, amino acids 239–249 (SEQ ID NO 57) in the $Fc_{\gamma 1}1$–$Fc_{\gamma 1}2$ hinge region and amino acids 291–305 (SEQ ID NO 58), 329–337 (SEQ ID NO 59), and 349–352 (SEQ ID NO 35) in the $Fc_{\gamma 1}2$ domain of IgG1 are substituted by IgE residues 357–365 (SEQ ID NO 53), 407–420 (SEQ ID NO 11), 445–453 (SEQ ID NO 14), and 465–469 (SEQ ID NO 15), respectively, as described in the construction of IgGEL in Example 2 below.

The invention further provides for an IgE variant comprised of a human IgG1 template wherein the entire $Fc_{\gamma 1}2$ domain of IgG1 (amino acid residues 250–361) (SEQ ID NO 60) is replaced by the homologous $Fc_\epsilon 3$ domain of IgE (amino acid residues 366–497.) In a preferred embodiment, the IgG1 template contains, in addition to the entire $Fc_\epsilon 3$ domain of IgE, the $Fc_\epsilon 2$–$Fc_\epsilon 3$ hinge region of IgE (amino acid residues 357–365) (SEQ ID NO 53) in place of the homologous $Fc_{\gamma 1}1$–$Fc_{\gamma 1}2$ hinge region of IgG1 (amino acid residues 239–249) (SEQ ID NO: 57) as described in the construction of IgG2/EL in Example 1 below.

The invention also provides IgE antagonists comprising any immunoglobulin fragment containing the human IgE amino acid sequence(s) present in the chimeric heavy chain of any IgE variant described above. Preferably, the immunoglobulin fragment retains enough of the intact IgE variant's higher order structure to maintain the human IgE amino acid sequence(s) in a conformation analogous to that of native human IgE.

The IgE variants of the invention are optionally associated with other substances or are fused to additional polypeptide sequences. The polypeptides generally contain only IgE-homologous sequences, although they also may be fused to other polypeptides such as cytotoxic or immunosuppressive polypeptides. Cytotoxic polypeptides include IgG Fc effector sequences and polypeptide toxins such as diphtheria toxin or ricin A chain (U.S. Pat. Nos. 4,714,749 and 4,861,579). The immunoglobulin sequences fused to the IgE variant polypeptides herein include Fc or variable sequences of the heavy chains of IgG1, IgG2, IgG3, IgG4, IgE, IgM, IgD or IgA. Any IgE variant heavy chain fusion optionally is disulfide bonded in the ordinary fashion to heavy chains having the same sequence (thereby forming homodimers) or to different heavy chains (thereby forming heterodimers). In addition, the heavy chain hetero- or homodimers optionally are disulfide bonded to light chains in the fashion of native immunoglobulins.

In some embodiments, immunoglobulins comprising an IgE variant polypeptide will also comprise an immunoglobulin variable region. The antigenic specificity of the variable region is not critical. Suitable variable regions are those which are capable of binding haptens, or polypeptides or proteins from human, animal, plant, fungal, bacterial or insect sources. The specificity may be unknown or the variable region may have the ability to bind to a predetermined antigen.

In another embodiment, IgE variant polypeptides are covalently bound to a cytotoxic agent. For example, the polypeptide ricin D toxin isolated from the *Ricinus communis* plant can be bound to the carboxy terminus of the Fc domain, either by chemical means or, most preferably, by production of a fusion protein using standard recombinant DNA methods. This provides a means to selectively deliver the toxin only to cells expressing $Fc_\epsilon RI$ on their surfaces.

IV. Synthesis of IgE Variants

The foregoing IgE variants can be made by chemical synthesis of DNA encoding the desired IgE variant or by introducing mutations into DNA encoding a precursor form of the immunoglobulin molecule and expressing the DNA in recombinant cell culture or the like. The chemical synthesis of DNA is described above. The mutation of template immunoglobulin DNA is accomplished by conventional methods of oligonucleotide-mediated (site-directed) mutagenesis, PCR mutagenesis, and cassette mutagenesis of an earlier prepared DNA encoding a variant or a non-variant version of the immunoglobulin molecule. These techniques can utilize template-encoding nucleic acid (DNA or RNA), or nucleic acid complementary to the template-encoding nucleic acid.

Oligonucleotide-mediated mutagenesis is a preferred method for preparing IgE variant DNA. This technique is well known in the art, for example as described by Adelman et al., *DNA*, 2: 183 (1983). Briefly, the template DNA is altered by hybridizing an oligonucleotide encoding the desired mutation in the template, where the template is the single-stranded form of a plasmid or bacteriophage containing the unaltered template DNA. After hybridization, a DNA polymerase is used to synthesize an entire second complementary strand of the template that will thus incorporate the oligonucleotide primer, and will code for the selected alteration in the template DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. USA,* 75: 5765 (1978).

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the template immunoglobulin, and the other strand (the original template) encodes the unaltered sequence of the template immunoglobulin. This heteroduplex molecule is then transformed into a suitable host cell, usually a prokaryote such as *E. coli* JM101. The cells are plated onto agarose plates, and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding template immunoglobulin mutants at more than one site may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making IgE variants. While the following discussion refers to DNA, it is understood that the technique also finds application with RNA. The PCR technique generally refers to the following procedure (see Erlich, supra, the chapter by R. Higuchi, p. 61–70). When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

Another method for preparing variants, cassette mutagenesis, is based on the technique described by Wells et al., *Gene,* 34: 315 (1985).

Following the construction of DNA encoding the IgE variant of interest, the DNA is inserted into an expression vector, a suitable host cell is transformed with the recombinant vector, the transformed host cells are cultured and the recombinant IgE variant is recovered from the cell culture as described in the recombinant production of IgE peptide antagonist in Section II above. The IgE variant can then be screened for the ability to bind $Fc_eRI$ or other desired activity by using the same methods as those described in the screening of IgE peptide antagonists in Section II above.

V. Therapeutic, Diagnostic and Preparatory Uses of IgE Antagonists

The IgE antagonists of the invention are used in diagnostic and therapeutic indications. For example, in in vitro diagnostic assays they are employed as specific binding reagents in assays for Fc$_\epsilon$RI. The compounds of this invention are labelled with a detectable substance such as an enzyme, fluorescent or chemiluminescent group, radioisotope or a specific binding moiety that binds to a detectable substance (such as an enzyme). A typical specific binding moiety is an immunoglobulin variable domain which is capable of binding to the detectable substance. IgE variants comprising immunoglobulin variable domains are described in more detail above.

Assay systems that employ the IgE antagonists of this invention are analogous to the sandwich-type systems heretofore generally used in the immunoassay field. Here, the specific antagonist is employed in the same fashion as labelled antibodies directed against antigen (the Fc$_\epsilon$RI receptor) or as an absorption agent insolubilized on a matrix for the isolation of receptor from test sample. Redox, proteolytic, esterolytic or other conventional enzyme labels are conjugated to the compounds of this invention for use in conventional assay systems.

The IgE antagonists of this invention are also used in the isolation of Fc$_\epsilon$RI from cell culture in preparing Fc$_\epsilon$RI for therapeutic or research purposes. The antagonist is covalently bonded or noncovalently adsorbed to a matrix such as an ion exchange resin, an immunoaffinity column (containing an antibody capable of binding a polypeptide fused to the IgE antagonist), an immobilized antigen (where the IgE antagonist comprises an immunoglobulin variable region capable of binding to the antigen) or a cyanogen bromide activated polysaccharide. The immobilized IgE antagonist then is contacted with the receptor preparation under conditions such that the receptor is bound to the IgE antagonist. The receptor then is eluted by changing the pH or ionic conditions and separating the polypeptide preparation from the receptor.

In addition, the IgE antagonists of the invention can be used to raise antibodies against specific sites in the Fc$_\epsilon$RI-binding domain of IgE. Polyclonal antibodies to an IgE antagonist are generally raised in animals by multiple subcutaneous (sc) or intraperitoneal (ip) injections of the IgE antagonist and an adjuvant. It can be useful to conjugate the IgE antagonist or a fragment thereof containing the amino acid sequence of the desired antigenic site to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl$_2$, or R$^1$N=C=NR, where R and R$^1$ are different alkyl groups.

Animals ordinarily are immunized against the immunogenic conjugates of IgE antagonist with monophosphoryl lipid A (MPL)/trehalose dicorynomycolate (TDM) (Ribi Immunochem. Research, Inc., Hamilton, Mont.) and injecting the solution intradermally at multiple sites. Two weeks later the animals are boosted with the original amount of conjugate in MPL/TDM. 7 to 14 days later animals are bled and the serum is assayed for anti-IgE antagonist titer. Animals are boosted until the titer plateaus. Preferably, the animal is boosted with the conjugate of the same IgE antagonist, but conjugated to a different protein and/or through a different cross-linking agent. Conjugates also can be made in recombinant cell culture as protein fusions. Also, aggregating agents such as alum are used to enhance the immune response.

Monoclonal antibodies are prepared by recovering spleen cells from immunized animals and immortalizing the cells in conventional fashion, e.g. by fusion with myeloma cells or by Epstein-Barr (EB)-virus transformation and screening for clones expressing the desired antibody. The hybridoma technique described originally by Koehler and Milstein, *Eur. J. Immunol.*, 6: 511 (1976) and also described by Hammerling et al., In: *Monoclonal Antibodies and T-Cell Hybridomas*, Elsevier, N.Y., pp. 563–681 (1981) has been widely applied to produce hybrid cell lines that secrete high levels of monoclonal antibodies against many specific antigens.

The hybrid cell lines can be maintained in vitro in cell culture media. The cell lines producing the antibodies can be selected and/or maintained in a medium containing hypoxanthine-aminopterin thymidine (HAT). In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant or ascites fluid by conventional methods such as immune precipitation, ion-exchange chromatography, affinity chromatography such as protein A/protein G column chromatography, or the like. The antibodies described herein are also recovered from hybridoma cell cultures by conventional methods such as precipitation with 50% ammonium sulfate. The purified antibodies can then be sterile filtered.

The IgE antagonists herein can also be used in screening antibodies specific to the Fc$_\epsilon$RI-binding domain of IgE. For example, antibodies capable of binding specifically to the Fc$_\epsilon$RI-binding domains of IgE are selected by first immunizing a subject with IgE. Monoclonal antibodies are selected in the ordinary way for native IgE binding, and the monoclonal antibodies are then screened to identify those that bind to an IgE antagonist of this invention. Since the selected antibody is highly specific for the key site(s) involved in receptor binding it is then possible to reduce the size of the antibody; the bulk of the antibody is not needed for steric hinderance of the IgE-receptor interaction. Thus, it becomes feasible in allergy therapy to use anti-IgE monovalent antibodies or other anti-IgE fragments such as Fab, Fab' and the like.

The IgE antagonists of the invention can be used in the methods for diagnosing allergy disclosed and claimed in copending U.S. Ser. No. 08/165,436 filed Dec. 10, 1993. These methods use IgE antagonist inhibition of IgE/Fc$_\epsilon$RI binding to assist in the detection of IgE in a patient serum sample.

The IgE antagonists of the invention are used in therapies for the treatment or prophylaxis of allergies, although the IgE antagonist subgroup which bears cytotoxic functionalities is not considered suitable for therapy since it could lead to degranulation of mast cells and basophils. Otherwise, the IgE antagonists typically are administered to a patient who is known to be sensitized to an allergen, preferably prior to an acute allergic response.

The present invention also provides pharmaceutical compositions containing an effective amount of compounds of the present invention, including the nontoxic salts, amides and esters thereof, which may, alone, serve to provide the above-recited therapeutic benefits. Such compositions can be provided together with physiologically tolerable liquid, gel or solid diluents, adjuvants and excipients.

Typically, such pharmaceutical compositions are prepared as injectable liquid solutions or suspensions. Compositions may also be emulsified. The active ingredient is often mixed with diluents or excipients which are physiologically tolerable and compatible with the active ingredient. Suitable diluents and excipients are, for example, water saline, dextrose, glycerol, or the like, and combinations thereof. In addition, if desired the compositions may contain minor amounts of auxiliary substances such as wetting or emulsifying agents, stabilizing or pH-buffering agents, and the like. For a more detailed description of the foregoing see a standard pharmaceutical text such as Remington's Pharmaceutical Sciences, Mack Publishing Co. Easton, Pa. (1970).

The pharmaceutical compositions of this invention are conventionally administered parenterally by injection, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient in the range of 0.5% to 10% preferably 1%–2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders, and contain 10%–95% if active ingredient, preferably 25%–70%.

The peptide compounds of the invention may be formulated into the compositions as neutral or salt forms. Pharmaceutically acceptable nontoxic salts include the acid salts (formed with the free amino groups) and which are formed with inorganic acids such as, for example, hydrochloric or phosphoric acids, or organic acids such as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropyl amine, 2-ethylamino ethanol, histidine, procaine, and the like.

The dosages and administration route will depend upon the accessory functionalities accompanying the polypeptides (e.g. cytotoxic agents, immunoglobulin effector functions, etc.), the condition of the patient (including the population of mast cells and basophils), the half-life of the polypeptide, the affinity of the polypeptide for its receptor and other parameters known to the clinician. As a general guide in the case of IgE antagonist, one will determine from blood tests the amount of target cells circulating in the patient and determine the amount of antagonist to displace or effectively compete with endogenous IgE taking into account the population of $Fc_\epsilon RI$ receptors as well as the half life and affinity of the IgE antagonist for $Fc_\epsilon RI$. An excess of IgE antagonist calculated to be necessary to substantially displace native $Fc_\epsilon RI$-bound IgE over a reasonable therapeutic interval will then be administered.

Therapeutic IgE antagonists are administered by intravenous intrapulmonary, intraperitoneal subcutaneous or other suitable routes. Typically, the IgE antagonists are administered subcutaneously or intravenously over a period of about from 1 to 14 days as required, in amounts of about 2 to 3 mg/kg, for the treatment of acute allergic symptoms. In the prophylactic treatment of allergy, IgE antagonists are administered s.c. or i.v. about once a week for periods of about one or two months up to several years, in amounts of about 2 to 3 mg/kg. In the case of treatments with IgE variant polypeptides it is desirable to administer polypeptide in a dosing regimen sufficient to achieve a 2:1 molar ratio of polypeptide to basophil and mast cell surface $Fc_\epsilon RI$ receptor. It is well within the skill of the clinician to determine the amount of IgE antagonist needed to inhibit or suppress IgE binding to mast cells and basophils such that the release of histamine and other factors which are responsible for clinical hypersensitivity and anaphylaxis is prevented or reduced. Candidate doses are readily determined by the use of in vitro cell cultures or animal models.

Therapy of allergic disorders with IgE antagonist polypeptides can be combined with other known therapies for allergies. These include administration of gamma interferon, allergen desensitization, reduction in exposure to allergen, treatment with anti-histamines and the like.

Further details of the invention can be found in the following examples, which further define the scope of the invention. All references cited herein are expressly incorporated by reference in their entireties.

EXAMPLE 1

1. Materials and Methods

The human IgE gene was isolated as follows from a U266 cell line (K. Nilsson, H. Bennich, S. G. O. Johansson, J. Ponten, Clin. Exp. Immunol. 7, 477 (1970); J. G. Flanagan, T. H. Rabbitts, EMBO J. 1, 655 (1982); M. Seno et al., Nucl. Acids Res. 11, 719 (1983)) library prepared at Genentech. A cDNA library was generated from mRNA derived from the U266 cell line. PCR oligonucleotide primers coding for the N-terminal and the C-terminal portions of human $Fc_\epsilon$ were used to amplify the cDNA coding for the human IgE constant domains. The PCR products were digested with appropriate restriction enzymes and purified on acrylamide gels. The DNA fragments were ligated into pUC119 vectors that had been digested with the appropriate restriction enzymes. The heavy chain was then assembled with the DNA coding for the $V_H$ domain of the murine anti-p185$^{HER2}$ antibody, described in Carter et al., Proc. Nat. Acad. Sci. U.S.A., 89: 4285 (1992), according to the following procedure.

pDH160 is a pRK-based plasmid (derived from a phagemid vector containing a human cytomegalovirus enhancer and promoter, a 5' intron and SV40 polyadenylation signal described in C. M. Gorman, D. R. Gies, G. McCray, DNA & Prot. Eng. Techniques 2, 3 (1990)) containing DNA coding for the murine 4D5 $V_H$ region (Carter et al., supra) and DNA coding for the human IgG1 constant region (Capon et al., Nature, 337: 525–531 (1989)). pDH160 was digested with BstEII/HindIII to remove the region encoding the human IgG1 constant domains. Two fragments were then ligated into this backbone. The first fragment was a BstEII/SstI fragment encoding the N-terminal half of the human IgE constant region and the second fragment was an SstI/HindIII fragment encoding the C-terminal half of the human IgE constant region. The portion of this plasmid encoding the murine 4D5 $V_H$ and human IgE constant regions was sequenced and the sequence was found to match the human IgE constant sequences reported in Kabat et al.

Mutagenesis of the human IgE gene was performed according to the method of Kunkel (T. A. Kunkel, Proc. Natl. Acad. Sci. U.S.A. 82, 488 (1985)) using buffers and enzymes supplied with a commercially available in vitro mutagenesis kit (BioRad). Sequences of the variant IgE DNAs were checked using dideoxynucleotide sequencing. For each IgE variant, 293S cells were transfected by the calcium phosphate method described in Gorman et al., DNA & Prot. Eng. Techniques 2, 3 (1990), washed with phosphate-buffered saline (PBS), and supernatant was collected between 48 and 96 hours and concentrated using a Centriprep 30 (Amicon). IgE variants were examined by SDS-PAGE to ascertain correct molecular weight and were quantified by ELISA using purified human IgE as the reference standard.

A murine anti-human IgE antibody, MaE1 (Genentech), was used to capture IgE in the ELISA. MaE1 was chosen from a panel of antibodies which mapped outside the $Fc_\epsilon RI$ binding site on IgE, i.e., not on domain $Fc_\epsilon 3$. IgE was detected with an HRP goat anti-human IgE (Kirkegaard & Perry Labs). IgE concentrations were extrapolated by nonparametric linear regression analysis. Initially, IgE variants were affinity-purified with another murine anti-human IgE antibody, MaE2 (Genentech), coupled to CNBr-Sepharose (Pharmacia). Since assays using either purified or non-purified IgE gave identical results, the purification step was eliminated for other variants.

Indirect immunofluorescence analysis of IgE binding to $Fc_\epsilon RI$ α-chain on stable, transfected CHO 3D10 cells (obtained as described in Hakimi et al., *J. Biol. Chem.*, 265: 22079 (1990)) was performed as follows. $5\times10^5$ cells in PBS containing 0.1% BSA-10 mM sodium azide were incubated for 30 min. at 4° C. with 0.1–10 mg/ml IgE or IgG1 control (humanized anti-p185$^{HER2}$ IgG1, P. Carter et al., *Proc. Natl. Acad. Sci. U.S.A.* 89, 4285 (1992)). After washing, the cells were incubated for 30 min. at 4° C. with 20 mg/ml affinity-purified FITC-conjugated rabbit anti-human IgE (Axell) or goat FITC-F(ab)'$_2$ anti-human IgG (Organon Teknica catalog number 10711-0081), respectively. Analyses were performed on a FACSCAN flow cytometer (Becton Dickinson) using FACSCAN LYSIS software. Percent positive cells were calculated using standard one-parameter analysis measuring relative fluorescence intensity compared to the IgG1 control. From the titration curve (0.1–10 mg/ml), binding of variant IgE was determined as the percent of binding relative to human IgE at 1 mg/ml, this concentration being on the steep portion of the titration curve (FIG. 1).

Variants which exhibited reduced binding were also assayed by ELISA using recombinant $Fc_\epsilon RI$ α-chain-coated plates to verify their reduced binding relative to native IgE.

2. Results

The initial variants of human IgE were designed by taking advantage of the fact that human IgG1 does not bind to IgE receptors ( M. Weetall, B. Shopes, D. Holowka, B. Baird, *J. Immunol.* 145, 3849 (1990)). Using homology scan methodology described in B. C. Cunningham, P. Jhurani, P. Ng, J. A. Wells, *Science* 243, 1330 (1989), five $Fc_\epsilon 3$ loops were replaced with their counterparts from human IgG1 $Fc_\gamma 2$ as described in Table 3 below. The sixth loop (DE), which contains a conserved, structurally important glycosylation site in both IgE and IgG, was not altered. Additional variants were evaluated in which solvent exposed residues in $Fc_\epsilon 3$ β-strands and selected loops in $Fc_\epsilon 2$ and $Fc_\epsilon 4$ were changed to alanine, as opposed to IgG1 homology replacements, in order to maximize the effect of altering only 2–3 sidechains per variant (Table 3). Based on the results from these variants, a second set of variants was constructed to characterize individual residues within the regions found to affect the $Fc_\epsilon RI$-IgE interaction. Residues were changed to alanine or to other amino acids in order to determine if size, charge, hydrogen-bonding capability or hydrophobicity were important for a particular residue.

TABLE 3

Binding of IgE variants to human $Rc_\epsilon RI$.

| | | | | $Fc_\epsilon RI$ Binding | | | | |
|---|---|---|---|---|---|---|---|---|
| | | | | 3D10 Cells % binding at 1 mg/ml | | | ELISA Assay $IC_{50}$ | |
| Variant | Kabat residue number | Human IgE sequence | Variant sequence | Mean | S.D. | N | Mean | N |
| $Fc_\epsilon 3$ Loop AB | | | | | | | | |
| 1 | 377–385 | FDLFIRKS (SEQ ID NO 21) | KDTLMISRT (SEQ ID NO 22) | 3 | 1 | 5 | | |
| 2 | 377–385 | FDLFIRKS (SEQ ID NO 21) | KDLMISRT (SEQ ID NO: 23) | 8 | 1 | 10 | 0 | 1 |
| 3 | 377 | F | A | 100 | | 1 | | |
| 4 | 377 | F | K | 98 | 2 | 5 | 100 | 2 |
| 5 | 381 | F | A | 10 | 2 | 7 | | |
| 6 | 381 | F | M | 28 | 8 | 7 | 3 | 2 |
| 7 | 382 | I | A | 91 | 20 | 3 | | |
| 8 | 383–385 | RKS | AAA | 104 | 6 | 5 | | |
| 9 | 383, 384 | RK | DD | 89 | | 2 | 73 | 2 |
| $Fc_\epsilon 3$ Loop BC | | | | | | | | |
| 10 | 396–401 | APSKGT (SEQ ID NO 24) | SHEDPQ (SEQ ID NO 25) | 66 | 20 | 16 | | |
| 11 | 396–401 | A (P) SK (G) T (SEQ ID NO 24) | S (P) ED (G) Q (SEQ ID NO 26) | 77 | 6 | 9 | | |
| 12 | 398–401 | SK (G) T (SEQ ID NO 27) | AA (G) A (SEQ ID NO 28) | 98 | 10 | 7 | | |
| $Fc_\epsilon 3$ Loop CD | | | | | | | | |
| 13 | 407–420 | SRASGKPVNHS (SEQ ID NO 11) | YVDGVQVHNAK (SEQ ID NO 29) | 35 | 15 | 8 | | |
| 14 | 407–415 | SR (A) S (G) K (SEQ ID NO 30) | AA (A) A (G) A (SEQ ID NO 31) | 33 | 6 | 3 | | |
| 15 | 407 | S | A | 106 | | 1 | | |
| 16 | 407 | S | E | 102 | 14 | 4 | 70 | 2 |
| 17 | 408 | R | A | 84 | 7 | 12 | | |
| 18 | 408 | R | E | 12 | 4 | 6 | 0 | 2 |
| 19 | 408 | R | Q | 50 | 11 | 9 | 22 | 3 |
| 20 | 408 | R | K | 92 | 15 | 6 | | |

TABLE 3-continued Binding of IgE variants to human Fc$_\epsilon$RI.

|  |  |  |  | Fc$_\epsilon$RI Binding | | | | |
|---|---|---|---|---|---|---|---|---|
|  |  |  |  | 3D10 Cells % binding at 1 mg/ml | | | ELISA Assay IC$_{50}$ | |
| Variant | Kabat residue number | Human IgE sequence | Variant sequence | Mean | S.D. | N | Mean | N |
| 21 | 411 | S | A | 69 | 1 | 4 |  |  |
| 22 | 411 | S | Q | 28 | 12 | 14 | 10 | 2 |
| 23 | 415 | K | A | 118 |  | 1 |  |  |
| 24 | 415 | K | D | 66 | 3 | 8 |  |  |
| 25 | 418 | N | A | 97 | 9 | 5 |  |  |
| 26 | 419 | H | A | 98 | 4 | 5 |  |  |
| 27 | 420 | S | A | 97 | 8 | 4 | 94 | 1 |
| Fc$_\epsilon$3 Loop EF | | | | | | | | |
| 28 | 445–453 | TRDWIEGET (SEQ ID NO 14) | HQDWLDGKE (SEQ ID NO 32) | 11 | 6 | 6 | 0 | 2 |
| 29 | 445, 446 | TR | AA | 88 | 9 | 12 |  |  |
| 30 | 445 | T | A | 99 | 17 | 10 |  |  |
| 31 | 446 | R | A | 95 | 7 | 9 |  |  |
| 32 | 446 | R | E | 74 | 14 | 4 | 133 | 4 |
| 33 | 447 | D | A | 99 | 6 | 21 | 96 | 2 |
| 34 | 447 | D | R | 41 | 21 | 7 | 0 | 4 |
| 35 | 447 | D | N | 95 | 8 | 3 | 71 | 2 |
| 36 | 447 | D | E | 92 | 9 | 5 | 120 | 1 |
| 37 | 450–453 | E (G) ET (SEQ ID NO 33) | A (G) AA (SEQ ID NO 34) | 19 | 7 | 8 | 0 | 2 |
| 38 | 450 | E | A | 96 | 8 | 11 | 85 | 2 |
| 39 | 450 | E | R | 104 | 10 | 4 | 68 | 2 |
| 40 | 452 | E | A | 60 | 26 | 19 | 14 | 4 |
| 41 | 452 | E | R | 14 | 7 | 14 | 0 | 4 |
| 42 | 452 | E | Q | 13 | 3 | 13 | 0 | 3 |
| 43 | 452 | E | D | 103 | 5 | 10 | 116 | 3 |
| 44 | 453 | T | R | 100 | 3 | 5 | 133 | 3 |
| 45 | 453 | T | Y | 62 | 3 | 5 | 45 | 2 |
| Fc$_\epsilon$3 Loop FG | | | | | | | | |
| 46 | 465–469 | RALM (SEQ ID NO 15) | APIE (SEQ ID NO 33) | 73 | 11 | 15 |  |  |
| 47 | 465, 469 | R (AL) M (SEQ ID NO 15) | A (AL) E (SEQ ID NO 52) | 43 | 7 | 9 | 86 | 3 |
| 48 | 465 | R | E | 27 | 9 | 14 | 64 | 2 |
| 49 | 469 | M | A | 73 | 8 | 9 | 78 | 3 |
| Fc$_\epsilon$3 β-str B | | | | | | | | |
| 50 | 387, 389 | T (I) T | A (I) A | 83 | 7 | 5 | 77 | 2 |
| 51 | 387 | T | A | 120 |  | 2 |  |  |
| 52 | 389 | T | A | 138 |  | 1 |  |  |
| Fc$_\epsilon$3 β-str C | | | | | | | | |
| 53 | 403, 405 | N (L) T | A (L) A | 105 | 11 | 5 |  |  |
| Fc$_\epsilon$3 β-str D | | | | | | | | |
| 54 | 423–428 | KEEKQR (SEQ ID NO 36) | PREQQY (SEQ ID NO 37) | 2 | 1 | 10 |  |  |
| 55 | 423–428 | KEEKQR (SEQ ID NO 36) | AEAKAR (SEQ ID NO 38) | 95 | 10 | 5 |  |  |
| 56 | 423–428 | KEEKQR (SEQ ID NO 36) | KAEAQA (SEQ ID NO 39) | 41 | 17 | 7 | 67 | 1 |
| 57 | 422 | R | A | 99 | 11 | 7 |  |  |
| 58 | 423–425 | KEE | AAA | 100 | 2 | 8 | 66 | 1 |
| 59 | 423 | K | P | 2 | 1 | 8 |  |  |
| 60 | 426–428 | KQR | AAA | 60 | 12 | 10 | 42 | 2 |
| 61 | 426 | K | A | 76 | 13 | 5 |  |  |
| 62 | 427 | Q | A | 92 | 12 | 7 |  |  |
| 63 | 428 | R | A | 42 | 13 | 7 | 69 | 1 |
| Fc$_\epsilon$3 β-str E | | | | | | | | |
| 64 | 438, 440 | T (S) T | A (S) A | 84 | 19 | 11 |  |  |
| Fc$_\epsilon$3 β-str F | | | | | | | | |
| 65 | 455–459 | Q (C) R (V) T (SEQ ID NO 40) | A (C) A (V) A (SEQ ID NO 41) | 96 | 9 | 15 | 84 | 1 |
| 66 | 460 | H | D | 77 | 9 | 8 | 92 | 1 |
| 67 | 462 | H | D | 90 | 2 | 4 | 140 | 1 |
| Fc$_\epsilon$3 β-str G | | | | | | | | |
| 68 | 471, 473 | S (T) T | A (T) A | 107 | 7 | 4 |  |  |
| Fc$_\epsilon$2 | | | | | | | | |
| 69 | 329–336 | QKH (WL) SDR (SEQ ID NO 42) | AAA (WL) AAA (SEQ ID NO 43) | 107 | 8 | 4 |  |  |
| 70 | 361–365 | D (S) N (P) R (SEQ ID NO 44) | A (S) A (P) A (SEQ ID NO 45) | 67 | 19 | 14 |  |  |

TABLE 3-continued

Binding of IgE variants to human Fc$_\epsilon$RI.

| | Kabat residue | | | Fc$_\epsilon$RI Binding | | | | |
|---|---|---|---|---|---|---|---|---|
| | | | | 3D10 Cells % binding at 1 mg/ml | | | ELISA Assay IC$_{50}$ | |
| Variant | number | Human IgE sequence | Variant sequence | Mean | S.D. | N | Mean | N |
| Fc$_\epsilon$4 | | | | | | | | |
| 71 | 498–501 | PRAA (SEQ ID NO 46) | QPRE (SEQ ID NO 47) | 89 | 12 | 4 | | |
| 72 | 594–599 | ASPSQT (SEQ ID NO 48) | LHNHY (SEQ ID NO 49) | 92 | 1 | 4 | | |
| 73 | 595–599 | S (P) SQT (SEQ ID NO 50) | A (P) AAA (SEQ ID NO 51) | 80 | 11 | 5 | | |

The binding of human IgE variants as measured by immunofluorescence using a CHO 3D10 cell line expressing the human Fc$_\epsilon$RI receptor α-chain is shown in Table 3 (homology scan sequences are italicized) and FIG. 1. The binding values shown in Table 3 are expressed in terms of percent binding compared to the binding of native human IgE to human $Fc_{\epsilon}RI$ receptor α-chain. Though the $Fc_{\epsilon}RI$ receptor is comprised of one α-chain, one β-chain and two γ-chains, J. Hakimi et al., *J Biol. Chem.* 265, 22079 (1990) showed that the α-chain is sufficient for IgE binding.

3. Discussion

Individual residue replacement in loop AB and β-strand D showed that in both cases only a single amino acid participated in binding. In loop AB, only substitutions at Phe381 had an effect (variants 5 and 6, Table 3). In β-strand D, the single amino acid change Lys423Pro abolished binding to the same extent as did replacement of the entire loop (variants 54 and 59, Table 3). However, the Lys sidechain is not involved in binding since replacing the Lys423 residue with Ala had no affect on binding (variant 58, Table 3). Arg428Ala was another single amino acid change in β-strand D that effected a reduction in binding.

In loop CD, Arg408 was determined to be the most important binding residue. Arg408Ala and Arg408Lys had little affect on binding but Arg408Glu and Arg408Gln reduced binding by 88% and 50%, respectively. The latter two variants demonstrated that a positive charge at this position is important. Replacements at two other residues in loop CD also affected binding. Lys415Asp reduced binding by 34%, much less than for the charge exchange at Arg408, and at Ser411 Ala and Gln substitutions diminished binding by 31% and 72%, respectively.

In loop EF, Asp447 and Glu452 were determined to be the most important binding residues. At Asp447, removal of the sidechain (Asp447Ala), repositioning the negative charge (Asp447Glu), or neutralization of the charge (Asp447Asn) had no affect, but charge reversal (Asp447Arg) reduced binding by 59%. In contrast to residue 447, removal of the sidechain at residue 452 (Glu452Ala) reduced binding and charge neutralization (Glu452Gln) was as deleterious as charge reversal (Glu452Arg). Repositioning the negative charge (Glu452Asp) had no affect. Side chain bulk was determined to be important at position 453. Thr453Arg had no affect while Thr453Tyr reduced binding. The Arg sidechain was able to move out of the way during $Fc_{\epsilon}RI$-IgE binding whereas the bulkier, less mobile Tyr sidechain could not and thereby sterically hindered the $Fc_{\epsilon}RI$-IgE interaction.

Two other regions were determined to be involved in IgE binding. In loop FG, the charge reversal Arg465Glu significantly reduced binding by 73% while Met469Ala reduced binding only 27%. The Arg405Glu variant demonstrated that Arg465 plays a dominant role in loop FG. In the hinge region between domains $Fc_{\epsilon}2$ and $Fc_{\epsilon}3$, three residues - - - 361, 363, 365 - - - were simultaneously changed to Ala (variant 70) and binding to $Fc_{\epsilon}RI$ was reduced by 33%.

EXAMPLE 2

1. Materials and Methods

A phagemid vector encoding a humanized anti-$p^{185HER2}$ IgG1 (with a 5' intron, SV40 polyadenylation signal, and a human cytomegalovirus enhancer and promoter) was obtained as described in P. Carter et al., *Proc. Natl. Acad. Sci. U.S.A.* 89, 4285 (1992). Mutagenesis of the humanized anti-$p185^{HER2}$ IgG1-encoding DNA was performed according to the method of A. Kunkel, *Proc. Natl. Acad. Sci. U.S.A.* 82, 488 (1985) using buffers and enzymes supplied with a commercially available in vitro mutagenesis kit (BioRad). Sequences of the chimeric (variant IgE) DNAs obtained were checked using dideoxynucleotide sequencing. For each IgE variant, 293S cells were transfected by the calcium phosphate method described in C. M. Gorman, D. R. Gies, G. McCray, *DNA & Prot. Eng. Techniques* 2, 3 (1990), washed with phosphate-buffered saline (PBS), and supernatant was collected between 48 and 96 hours and concentrated using a Centriprep 30 (Amicon). IgE variants were examined by SDS-PAGE to ascertain correct molecular weight and were quantified by ELISA using humanized anti-$p185^{HER2}$ F(ab) as the reference standard.

A goat anti-human IgG F(ab) (organon Teknica catalog number 55010) was used to capture and an HRP-conjugated goat anti-human IgG F(ab) (Organon Teknica catalog number 55223) was used to detect IgE variants in the ELISA. IgE concentrations were extrapolated by non-parametric linear regression analysis.

Indirect immunofluorescence analysis of IgE variant binding to $Fc_{\epsilon}RI$ α-chain on stable, transfected CHO 3D10 cells was performed as described in Example 1 above. Goat FITC-$F(ab)'_2$ anti-human IgG (Organon Teknica cat. no. 55201) was used to detect binding in the immunofluorescence assays.

2. Results

To verify that the IgE residues determined in this study are indeed important for binding of IgE to $Fc_{\epsilon}RI$, two chimeric molecules were constructed. In the first chimera, IgG2/E3, the entire $Fc_\epsilon3$ domain and the $Fc_\epsilon2$-$Fc_\epsilon3$ hinge region of human IgE were substituted for the homologous $Fc_{\gamma1}2$ domain and $Fc_{\gamma1}1$–$Fc_{\gamma1}2$ hinge region, respectively, in a human IgG1 antibody. The IgG2/E3 variant was constructed by replacing the DNA encoding human IgG1 $Fc_{\gamma1}2$ residues Cys239-Gly361 (SEQ ID NO 55) with DNA encoding human IgE $Fc_\epsilon3$ residues Cys357-Gly497 (SEQ ID NO 56) according to the following procedure.

Polymerase chain reaction (PCR) was used to extract DNA coding for the $Fc_\epsilon3$ domain (residues Gly366-Gly497) (SEQ ID NO 54) from the phagemid carrying human IgE constant region-encoding DNA described in Example 1 above. PCR was also used to extract DNA coding for the humanized murine 4D5 $V_H$ region and the $C_{\gamma1}1$ and hinge regions (residues Glu1-Gly249) of human IgG1 and to extract DNA coding for the $C_{\gamma1}3$ region (residues Gly361-Lys478) of human IgG1 from a phagemid carrying humanized anti-$p185^{HER2}$IgG1-encoding DNA (described in Carter et al., supra.) The PCR primers used in the various PCR reactions were designed to introduce unique restriction sites at the termini of the resulting PCR products such that the PCR products could be easily assembled into a single DNA coding for $V_H$-$C_{\gamma1}1$-IgG1 hinge-$C_\epsilon3$-$C_{\gamma1}3$. Accordingly, the three PCR products were digested with restriction enzymes to create the desired 5' overhangs. The digested PCR products were melted and the resulting single-stranded fragments were annealed and ligated to create a single DNA coding for $V_H$-$C_{\gamma1}1$-IgG1 hinge-$C_\epsilon3$-$C_{\gamma1}3$. Next, this DNA fragment was amplified by PCR and then ligated into the phagemid vector described in Carter et al., supra. Finally, site directed mutagenesis (Kunkel, supra) was employed to replace the IgG1 hinge (human IgG1 residues 239–249) (SEQ ID NO 57) with the $Fc_\epsilon2$-$Fc_\epsilon3$ hinge (human IgE residues 357–365) (SEQ ID NO 53). The DNA insert in the recombinant vector was sequenced using the dideoxynucleotide method.

In the second chimera, IgGEL, only IgE loops critical to human IgE/$Fc_\epsilon$RI binding, i.e., loops CD, EF and FG, and (to a lesser extent) the $Fc_\epsilon2$-$Fc_\epsilon3$ hinge region, were substituted for homologous regions in human IgGI. Site-directed mutagenesis (Kunkel, supra) was used to introduce DNA encoding residues 407–420 (SEQ ID NO 11) of the $Fc_\epsilon3$ CD loop of human IgE, residues 445–453 (SEQ ID NO 14) of the $Fc_\epsilon3$ EF loop of human IgE, residues 465–469 (SEQ ID NO 15) of the $Fc_\epsilon3$ FG loop of human IgE, and residues 357–365 (SEQ ID NO 53) of the $Fc_\epsilon2$-$Fc_\epsilon3$ hinge of human IgE in place of DNA encoding human IgG1 residues 291–305 (SEQ ID NO 58), 329–337 (SEQ ID NO 59), 349–352 (SEQ ID NO 35), and 239–249 (SEQ ID NO 57), respectively, in the humanized anti-$p185^{HER2}$IgG1 phagemid described in Carter et al., supra.

FIG. 2 shows that IgG2/E3, which contained the entire $Fc_\epsilon3$ domain, bound about 4-fold less well ($EC_{50}$ 2.0 mg/ml) than native human IgE ($EC_{50}$ 0.5 mg/ml). And though binding of IgGEL was reduced compared to native IgE, IgGEL binding to $Fc_\epsilon$RI was significantly better than for the parent IgG, which did not bind at all (FIG. 2). In addition, a murine monoclonal antibody which binds to human IgE and blocks IgE binding to $Fc_\epsilon$RI, described in L. G. Presta et al., *J. Immunol.* 151, 2623 (1993), exhibited essentially the same binding ratios with IgG2/E3 and IgGEL that $Fc_\epsilon$RI exhibited with IgG2/E3 and IgGEL (FIG. 2).

3. Discussion

The ability of IgGEL to bind $Fc_\epsilon$RI and an anti-IgE antibody demonstrated the importance of IgE loops CD, EF and FG in the IgE-$Fc_\epsilon$RI interaction. Based on this result and the other results presented herein, it was determined that the $Fc_\epsilon3$ domain contains the major, if not complete, site for $Fc_\epsilon$RI binding of IgE. The IgE $Fc_\epsilon3$ domain is structurally homologous to the $C_\gamma2$ domain of IgG which plays a major role in the binding of IgG to its high affinity receptor, $Fc_\gamma$RI. The IgG-$Fc_\gamma$RI system, though, utilizes a more localized region on IgG consisting of the lower portion of the $C_\gamma1$–$C_\gamma2$ hinge (reported in A. R. Duncan, J. M. Woof, L. J. Partridge, D. R. Burton, G. Winter, *Nature* 332, 563 (1988) and R. Jefferis, J. Lund, J. Pound, *Mol. Immunol.* 27, 1237 (1990)) and, possibly, loop FG and β-strands F and G. In contrast, the IgE-$Fc_\epsilon$RI system was determined to utilize a much larger area for binding including loops CD, EF and FG.

We claim:

1. An IgE variant comprising an immunoglobulin template and binding determinant sequences $CD_{bds}$, $EF_{bds}$ and Arg-Ala-Leu-Met (SEQ ID NO: 15) which have been substituted for the analogous template sequences, wherein:

a) $CD_{bds}$ is selected from the group consisting of:
- Arg-Ala-Ser-Gly-Lys (SEQ ID NO: 1);
- Arg-Ala-Ser-Gly-Lys-Pro (SEQ ID NO: 2);
- Arg-Ala-Ser-Gly-Lys-Pro-Val (SEQ ID NO: 3);
- Arg-Ala-Ser-Gly-Lys-Pro-Val-Asn (SEQ ID NO: 4);
- Arg-Ala-Ser-Gly-Lys-Pro-Val-Asn-His (SEQ ID NO: 5);
- Arg-Ala-Ser-Gly-Lys-Pro-Val-Asn-His-Ser (SEQ ID NO: 6);
- Ser-Arg-Ala-Ser-Gly-Lys-Pro (SEQ ID NO: 7);
- Ser-Arg-Ala-Ser-Gly-Lys-Pro-Val (SEQ ID NO: 8);
- Ser-Arg-Ala-Ser-Gly-Lys-Pro-Val-Asn (SEQ ID NO: 9);
- Ser-Arg-Ala-Ser-Gly-Lys-Pro-Val-Asn-His (SEQ ID NO: 10); and Ser-Arg-Ala-Ser-Gly-Lys-Pro-Val-Asn-His-Ser (SEQ ID NO: 11);

b) $EF_{bds}$ is selected from the group consisting of:
Asp-Trp-Ile-Glu-Gly-Glu-Thr (SEQ ID NO: 12);
Arg-Asp-Trp-Ile-Glu-Gly-Glu-Thr (SEQ ID NO: 13); and
Thr-Arg-Asp-Trp-Ile-Glu-Gly-Glu-Thr (SEQ ID NO: 14).

2. The IgE variant of claim 1 wherein the IgE variant comprises the $CD_{bds}$ amino acid residues of 407–420 (Ser-Arg-Ala-Ser-Gly-Lys-Pro-Val-Asn-His-Ser) (SEQ ID NO: 11), the $EF_{bds}$ amino acid residues of 445–453 (Thr-Arg-Asp-Trp-Ile-Glu-Gly-Glu-Thr) (SEQ ID NO: 14), and 465–469 (Arg-Ala-Leu-Met) (SEQ ID NO: 15) of human IgE.

3. The IgE variant of claim 2 wherein the binding determinant sequences further comprise the $Fc_\epsilon 2$–$Fc_\epsilon 3$ hinge region residues 357–365 Cys-Ala-Asp-Ser-Asn-Pro-Arg (SEQ ID NO 53) of human IgE.

4. The IgE variant of claim 3 wherein the binding determinant sequences comprising the $Fc_\epsilon2$-$Fc_\epsilon3$ hinge region are residues 361–365 (SEQ ID NO: 44).

5. The IgE variant of claim 1 wherein the immunoglobulin template is selected from the group consisting of human or rat IgG, IgA, IgD and IgM.

6. The IgE variant of claim 2 wherein the immunoglobulin template is human IgG1.

7. The IgE variant of claim 6 defined by replacing the $Fc_\gamma1$–$Fc_\gamma2$ residues 250–361 (SEQ ID NO: 60) of IgG1 with $Fc_\epsilon3$ residues 366–497 (SEQ ID NO: 54) of IgE.

8. The IgE variant of claim 6 defined by replacing the IgG1 residues 239–249, Cys-Pro-Pro-Cys-Pro-Pro-Ala-Pro-Gul-Leu-Leu-Gly (SEQ ID NO: 53) in the $Fc_\gamma1$–$Fc_\gamma2$ region and residues 291–305, Thr-Val-Gly-Val-Gly-Val-His-Asn-Ala-Lys (SEQ ID NO: 58), 329–337, His-Gln-Asp-Trp-Leu-Asn-Gly-Lys-Glu (SEQ ID NO: 59) and 349–352, Ala-Pro-Ile-Glu (SQ ID NO: 35) in the $Fc_\gamma2$ domain of IgG1 with the IgE $Fc_\epsilon2$–$Fc_\epsilon3$ hinge region residues 357–365 (SEQ ID NO: 53), the $Fc_\epsilon3$ CD loop residues 407–420 (SEQ ID NO: 11), the $Fc_\epsilon3$ loop residues 445–453 (SEQ ID NO: 14), the $Fc_\epsilon3$ FG loop residues 465–469 (SEQ ID NO: 15), respectively.

* * * * *

UNITED STATES PATENT AND TRADEMARK OFFICE
CERTIFICATE OF CORRECTION

PATENT NO.    :    5,965,709

DATED         :    October 12, 1999

INVENTOR(S)   :    Leonard G. Presta, Paula M. Jardieu

It is certified that error appears in the above-identified patent and that said Letters Patent is hereby corrected as shown below:

In the Claim:

Under claim 8, line 3, before "region," please insert --hinge--.

Signed and Sealed this

Twenty-eighth Day of March, 2000

Attest:

Q. TODD DICKINSON

Attesting Officer

Commissioner of Patents and Trademarks